United States Patent [19]
You

[11] Patent Number: 5,976,805
[45] Date of Patent: Nov. 2, 1999

[54] *NEISSERIA GONORRHOEAE* SPECIFIC DNA FRAGMENT—GC3

[75] Inventor: Qimin You, Lutherville, Md.

[73] Assignee: Becton Dickinson and Company, Franklin Lakes, N.J.

[21] Appl. No.: 09/067,773

[22] Filed: Apr. 27, 1998

[51] Int. Cl.[6] .............................. C12Q 1/68; C12P 19/34; C07H 21/02; C07H 21/04
[52] U.S. Cl. ........................... 435/6; 435/91.2; 536/23.1; 536/24.32; 536/24.33
[58] Field of Search .............................. 435/6, 91.1, 91.2, 435/91.5; 536/23.1, 24.3, 24.32, 24.33

[56] References Cited

U.S. PATENT DOCUMENTS

| | | | |
|---|---|---|---|
| 4,900,659 | 2/1990 | Lo et al. | 435/6 |
| 5,108,895 | 4/1992 | Woods et al. | 435/6 |
| 5,173,401 | 12/1992 | Wolff et al. | 435/6 |
| 5,256,536 | 10/1993 | Miyada et al. | 435/6 |
| 5,378,606 | 1/1995 | Stern et al. | 435/6 |
| 5,389,515 | 2/1995 | Chmelo et al. | 435/6 |
| 5,432,271 | 7/1995 | Barns et al. | 536/24.32 |
| 5,453,355 | 9/1995 | Birkenmeyer et al. | 435/6 |
| 5,536,638 | 7/1996 | Rossau et al. | 435/6 |
| 5,550,040 | 8/1996 | Purohit et al. | 435/91.2 |
| 5,595,874 | 1/1997 | Hogan et al. | 435/6 |

FOREIGN PATENT DOCUMENTS

WO 89/03891  5/1989  WIPO.

OTHER PUBLICATIONS

Carrick, C.S. (embl55 Accession #U65994), 1996.
Watson, J.D. et al. Recombinant DNA, Scientific American Books, New York, pp. 67–69, 1992.
Buimer et al.; Detection of *Chlamydai trachomatis* and *Neisseria gonorrhoeae* by Ligase Chain Reaction–Based Assays with Clinical Specimens from Various Sites: Implications for Diagnostic Testing and Screening, *J. of Clinical Microbiology*, 34(10):2395–2400 (Oct. 1996).
Crotchfelt et al.; Detection of *Neiseria gonorrhoeae* and *Chlamydia trachomatis* in Genitourinary Specimens form Men and Women by a Coamplification PCR Assay, *J. of Clinical Microbiology*, 35(6):1536–1540 (Jun. 1997).
Herrmann et al.; Detection of *Neisseria gonorrhoeae* from Air–Dried Genital Samples by Single–Tube Nested PCR, *J. of Clinical Microbiology*, 34(10):2548–2551 (Oct. 1996).
Iwen et al.; Evaluation of Nucleic Acid–Based Test (PACE 2C) for Simultaneous Detection of *Chlamydia trachomatis* and *Neisseria gonorrhoeae* in Endocervical Specimens, *J. Clinical Microbiology*, 33(10):2587–2591 (Oct. 1995).
A E Jephcott; Microbiological Diagnosis of Gonorrhoea, *Genitourin Med*, 73:245–252 (1997).
Schoone et al.; Comparison of Dot Blot with in–situ Hybridization for the Detection of *Neisseria gonorrhoeae* in Urethral Exudate, *J. of Applied Bateriology*, 66:401–405 (1989).
Stary et al.; Comparison of Ligase Chain Reaction and Culture for Detection of *Neisseria gonorrhoeae* in Genital and Extragenital Specimens, *J. of Clinical Microbiology*, 35(1):239–242 (Jan. 1997).
Totten et al.; DNA Hybridization Technique for the Detection of *Neisseria gonorrhoeae* in Men with Urethritis, *The Journal of Infectious Diseases*, 148(3):462–471 (Sep. 1983).

*Primary Examiner*—Carla J. Myers
*Assistant Examiner*—Diana Johannsen
*Attorney, Agent, or Firm*—David W. Highet, Esq.

[57] ABSTRACT

Disclosed herein is a newly-identified DNA sequence from *Neisseria gonorrhoeae* designated GC3. Also disclosed are methods, oligonucleotide probes, amplification primers, and kits for the species-specific detection of *N. gonorrhoeae*. Preferably, *N. gonorrhoeae* is detected by amplifying the *N. gonorrhoeae* nucleic acids using the disclosed amplification primers, and then detecting the amplified nucleic acids. In a more preferred embodiment, *N. gonorrhoeae* nucleic acids are amplified and detected by thermophilic strand displacement amplification (tSDA). Also preferred are methods for detecting *N. gonorrhoeae* that are employed in conjunction with methods for detecting other sexually-transmitted pathogens, in particular, *Chlamydia trachomatis*.

34 Claims, 7 Drawing Sheets

FIG-1

GC3 sequence[1] (SEQ ID NO:2):

```
CGGCATACTG TACCATAGCG TTCGCCTGGT CCGCCAAACG GGAAATTGGC    50
GGCATAAGCA GGGAACTGCT CCTGCAAACC TTTGACGACA TTTTGATCTT   100
CATAAAACAA AATGGTTGCC GCGCCCACCT TAAACAGCTT CAATTTTTGC   150
GCGGTCGGTT CAAAACTGTC GGCAGGCACG ACGGCACGCA GCGCGTCTTC   200
GACAAATTGC CACACCTTAT ATATTGCGCC CCTTCTTAGG GACGCAATAT   250
ATAAGGGTAA TCCCATGCGT AACGCCGTAG GATTGGACAT ATCCAAGTTG   300
ACTTTTGACG CAACGGCCAT TGTCGGGCAAT GCCGAAATAT TCGGCAAAGT   350
TTGACAACGA TTCAAAAGGT TTAGATCAAT TTTCGGACCG GTTGAAAAGC   400
TTGGGATGTC AGAAT   415
```

[1]The STOP codon TAG at the end of the reading frame is underlined.

FIG-2A

| Consensus | CGGCATACTG TACCATAGCG TTCGCCTGGT CCGCCAAACG GGAAATTGGC | 50 |
|---|---|---|
| ATCC19424 | .......... .......... .......... .......... .......... | 50 |
| ATCC35541 | .......... .......... .......... .......... .......... | 50 |
| ATCC43069 | .......... .......... .......... .......... .......... | 50 |
| ATCC43070 | .......... .......... .......... .......... .......... | 50 |
| BDMS2900  | .......... .......... .......... .......... .......... | 50 |
| CDC111    | .......... .......... .......... .......... .......... | 50 |

| Consensus | GGCATAAGCA GGGAACTGCT CCTGCAAACC TTTGACGACA TTTTGATCTT | 100 |
|---|---|---|
| ATCC19424 | .......... .......... .......... .......... .......... | 100 |
| ATCC35541 | .......... .......... .......... .......... .......... | 100 |
| ATCC43069 | .......... .......... .......... .......... .......... | 100 |
| ATCC43070 | .......... .......... .......... .......... .......... | 100 |
| BDMS2900  | .......... .......... .......... .......... .......... | 100 |
| CDC111    | .......... .......... .......... .......... .......... | 100 |

| Consensus | CATAAAACAA AATGGTTGCC GCGCCCRCCT TAAACAGCTT CAATTTTTGC | 150 |
|---|---|---|
| ATCC19424 | .......... .......... ........A. .......... .......... | 150 |
| ATCC35541 | .......... .......... ........G. .......... .......... | 150 |
| ATCC43069 | .......... .......... ........G. .......... .......... | 150 |
| ATCC43070 | .......... .......... ........G. .......... .......... | 150 |
| BDMS2900  | .......... .......... ........G. .......... .......... | 150 |
| CDC111    | .......... .......... ........G. .......... .......... | 150 |

| Consensus | GCGGTCGGTT CAAAACTGTC GGCAGGCACG ACGGCACGCA GCGGGTCTTC | 200 |
|---|---|---|
| ATCC19424 | .......... .......... .......... .......... .......... | 200 |
| ATCC35541 | .......... .......... .......... .......... .......... | 200 |
| ATCC43069 | .......... .......... .......... .......... .......... | 200 |
| ATCC43070 | .......... .......... .......... .......... .......... | 200 |
| BDMS2900  | .......... .......... .......... .......... .......... | 200 |
| CDC111    | .......... .......... .......... .......... .......... | 200 |

FIG-2B

```
Consensus    GACAAATTGC CACACCTTAT ATATTGCGCC CCTTCTTAGG GACGCAATAT ATAAGGGTAA    260
ATCC19424    .......... .......... .......... .......... .......... ..........    260
ATCC35541    .......... .......... .......... .......... .......... ..........    260
ATCC43069    .......... .......... .......... .......... .......... ..........    260
ATCC43070    .......... .......... .......... .......... .......... ..........    260
BDMS2900     .......... .......... .......... .......... .......... ..........    260
CDC111       .......... .......... .......... .......... .......... ..........    260

Consensus    TCCCATGCGT AACRCCGTAG GATTGGAYAT ATCSAARYTG ACHTTTRACG CAWCSGCCAT    320
ATCC19424    .......... ..G....... .......... ....C..GT. ...T...G.. ........        320
ATCC35541    .......... ..A....... .......... ....C..GC. ...A...G.. ..A.G...        320
ATCC43069    .......... ..A....... .......... ....C..GC. ...A...G.. ..A.G...        320
ATCC43070    .......... ..A....... .......... ....C..GC. ...A...G.. ..T.C...        320
BDMS2900     .......... ..G....... ........T. ....G..AC. ...C...A.. ..T.C...        320
CDC111       .......... ..A....... .......C.. ....C..GC. ...A...G.. ..T.C...        320

Consensus    RGTCGGCAAW RCSGARYATT CGGCAAAGTT TGACAACGAT TCAAAAGGTT TAGATCAGTT    380
ATCC19424    T......... .T.G.C.AT. .......... .......... .......... ..........    380
ATCC35541    T......... .T.G.C.AT. .......... .......... .......... ..........    380
ATCC43069    G......... .A.A.G.GC. .......... .......... .......... ..........    380
ATCC43070    G......... .A.A.G.GC. .......... .......... .......... ..........    380
BDMS2900     T......... .T.G.C.AT. .......... .......... .......... ..........    380
CDC111       G......... .A.A.G.GC. .......... .......... .......... ..........    380

Consensus    TTCGGACCGG TTGAAAAGCT TGGGATGTCA GAAT                                414
ATCC19424    .......... .......... .......... ....                                414
ATCC35541    .......... .......... .......... ....                                414
ATCC43069    .......... .......... .......... ....                                414
ATCC43070    .......... .......... .......... ....                                414
BDMS2900     .......... .......... .......... ....                                414
CDC111       .......... .......... .......... ....                                414
```

FIG-3B

| | | | | |
|---|---|---|---|---|
| PL1 | 5' | GCT CCT GCA AAC CTT | 3' | (SEQ ID NO:11) |
| PL2 | 5' | CGG CAG GCA CGA C | 3' | (SEQ ID NO:12) |
| BL3 | 5' | GCC ATT GTC GGC AA | 3' | (SEQ ID NO:13) |
| PL3 | 5' | ATT CGG CAA AGT TTG A | 3' | (SEQ ID NO:14) |
| PR1 | 5' | CGC GGC AAC CAT TT | 3' | (SEQ ID NO:15) |
| PR2 | 5' | GCA ATA TAT AAG GTG TG | 3' | (SEQ ID NO:16) |
| BR2 | 5' | CTT ATA TAT TGC GTC C | 3' | (SEQ ID NO:17) |
| PR3 | 5' | TTC AAC CGG TCC GA | 3' | (SEQ ID NO:18) |
| BR3 | 5' | CTG ACA TCC CAA GC | 3' | (SEQ ID NO:19) |

FIG-4A

```
GC3L40N:  5' CGA TTC CGC TCC AGA CTT CTC GGG CTT CTT AGG GAC G   3'   (SEQ ID NO:20)
GC3L44N:  5' CGA TTC CGC TCC AGA CTT CTC GGG CTT CTT AGG GAC GC  3'   (SEQ ID NO:21)
GC3L46N:  5' CGA TTC CGC TCC AGA CTT CTC GGG CTT CTT AGG GAC GCA 3'   (SEQ ID NO:22)

GC3R42N:  5' ACC GCA TCG AAT GCA TGT CTC GGG GAT ATG TCC AAT CCT  3'  (SEQ ID NO:23)
GC3R44N:  5' ACC GCA TCG AAT GCA TGT CTC GGG GAT ATG TCC AAT CCT A 3' (SEQ ID NO:24)
GC3R48N:  5' ACC GCA TCG AAT GCA TGT CTC GGG GAT ATG TCC AAT CCT AC 3' (SEQ ID NO:25)
GC3R44N2: 5' ACC GCA TCG AAT GCA TGT CTC GGG ATA TGT CCA ATC CTA C 3'  (SEQ ID NO:26)
```

Bumpers:

```
GC3BL44: 5' AAT TGC CAC ACC TTA T        3'   (SEQ ID NO:27)
GC3BR46: 5' GAT GCG TCA AAT GTC A        3'   (SEQ ID NO:28)
GC3BR50: 5' GGA TGC GTC AAA TGT CA       3'   (SEQ ID NO:29)
```

Detectors:

```
GC3D1:   5' CGC AAT ATA TAA GGG T        3'   (SEQ ID NO:30)
GC3D1R:  5' ACC CTT ATA TAT TGC G        3'   (SEQ ID NO:31)
GC3D2:   5' AAT CCC ATG CGT AAC          3'   (SEQ ID NO:32)
GC3D2R:  5' GTT ACG CAT GGG ATT          3'   (SEQ ID NO:33)
```

FIG-4B

The selected GC3 tSDA system:

```
     GC3BL44                    GC3L46N
AATTGCCACACCTTATATATTGCGCCCCTTCTTAGGGACGCAATATATAAGGGT
AATCCCATGCGTAACGCCGTAGGATTGGACATATCCAAGTTGACTTTGACGCAAC
     GC3D2R             GC3R44N              GC3BR46
```

*NEISSERIA GONORRHOEAE* SPECIFIC DNA FRAGMENT— GC3

FIELD OF THE INVENTION

The present invention relates to methods for identifying microorganisms, in particular, methods and nucleic acid sequences for identifying *Neisseria gonorrhoeae* by nucleic acid amplification and nucleic acid hybridization.

BACKGROUND OF THE INVENTION

Neisseria gonorrhoeae, also called gonococci ("GC"), is the causative agent of gonorrhea. It is also one of the most prevalent sexually-transmitted bacterial pathogens worldwide; over 3 million cases are reported annually in the United States alone. GC invades and colonizes the mucosal surfaces of the urethra, cervix, rectum, throat and conjunctiva. GC is extremely sensitive to desiccation and temperature changes, and is almost exclusively transmitted by direct mucosal contact, such as during sexual intercourse. The sensitivity of the organism to drying and temperature changes has been problematic for diagnostic methods, particularly in less developed countries where specimens often need to be stored for long periods of time and/or transported to a diagnostic laboratory prior to analysis. Brock, BIOLOGY OF MICROORGANISMS 515–16 (3d ed., 1979); Jephcott, *Genitourin. Med.* 73, 245 (1997).

Gonorrhea remains a significant health problem worldwide, even in countries in which effective drug treatment is readily available. The symptomology of gonorrhea differs between infected males and females. In men, GC is most often manifested by a painful infection of the urethral canal. By contrast, in women, GC infection is often asymptomatic or causes only a mild vaginitis. Even in asymptomatic women, however, GC infection may result in pelvic inflammatory disease, infertility, and ectopic pregnancy. Asymptomatic female carriers may unintentionally spread the disease to their sexual partners and their newborns as the baby passes through the cervix and vaginal canal. Infants born to GC-infected women have an increased incidence of conjunctivitis and pneumonia. Iwen et al., *J. Clin. Microbiol.* 33, 2587 (1995). Early, rapid and inexpensive methods of identifying GC infection in potential carriers is essential to curbing the spread of this pathogen. Brock, BIOLOGY OF MICROORGANISMS 591–92 (3d ed., 1979); Crotchfelt et al., *J. Clin. Microbiol.* 35, 1536 (1997), Herrmann et al., *J. Clin. Microbiol.* 34, 2548(1996).

Conventional methods of identifying GC include gram staining, colony morphology, growth on selective media, and cytochrome oxidase testing. GC colonies are characterized as gram-negative, oxidase-positive, diplococci. Organisms from presumptively identified colonies of GC are frequently confirmed by sugar fermentation, fluorescent antibody staining, and/or coagglutination. Brock, BIOLOGY OF MICROORGANISMS (3d ed., 1979). However, such culture procedures are laborious, time consuming, and limited by the low viability of GC samples. Rapid and early identification of GC is desirable, especially in asymptomatic individuals, to slow the spread of the disease. In addition, because of the poor viability of stored GC specimens, diagnostic methods that avoid the culturing of viable organisms are advantageous.

To obviate the problems attendant to conventional diagnosis of GC, there have been attempts to develop nucleic acid based diagnostic methods for identifying GC.

Nucleic acid based diagnostic assays, such as Southern hybridization, offer rapid means of identifying microorganisms, usually in less than one day. Polymerase chain reaction (PCR)-based methods are even more sensitive and can sometimes provide results within hours. However, nucleic acid based methodologies are often fraught with drawbacks. Most of these methods are costly, are available for only a few species of microorganisms, and can resolve only one species per sample tested. Moreover, nucleic acid based assays require the development of oligonucleotide probes or primers that are specific for the microorganism of interest.

U.S. Pat. No. 5,536,638 to Rossau et al. teaches a method of identifying GC using a probe directed to a rRNA sequence. See also U.S. Pat. No. 5,432,271 to Barns et al., U.S. Pat. No. 5,389,515 to Chmelo et al., U.S. Pat. No. 5,378,606 to Stern et al., and U.S. Pat. No. 5,173,401 to Wolff et al. As many as 10,000 copies of the rRNA genes are present in bacteria; thus, diagnostic methods based on detection of the GC rRNA genes take advantage of this naturally-occurring amplification. American Society for Microbiology, DIAGNOSTIC MOLECULAR MICROBIOLOGY: PRINCIPLES AND APPLICATIONS (D. H. Persing et al., eds., 1993). In addition, the 16S or 23S rRNA genes are frequently used for probe development because variable regions exist within these highly conserved genes that can be used for species-specific detection. However, for certain organisms it may not be possible to derive highly specific and sensitive probes from the 16S and 23S rRNA genes, for instance, because their evolutionary nucleic acid sequence conservation is too high. Another consequence of the conserved character of these genes is that the differentiation of two organisms is often based on only one or a few mismatches in the target sequence, which puts constrains on the stringency of the hybridization. A slight deviation from these conditions might result in misidentification.

Totten et al., *J. Infectious Diseases* 148, 462 (1983), teaches a method of identifying GC in clinical specimens by detecting the "cryptic plasmid" commonly associated with GC. However, not all strains of GC contain the cryptic plasmid. The presence of this plasmid in different GC strains is highly variable, ranging from about 40% to about 96%, depending on geographic location. Thus, this identification method is of limited utility.

U.S. Pat. No. 5,256,536 to Miyada et al. teaches a method for detecting GC using a nucleic acid probe. The probe was identified after subtractive hybridization of GC DNA by *N. meningitidis* DNA.

U.S. Pat. No. 5,453,355 to Birkenmeyer et al. concerns oligonucleotide primers and probes for detecting GC by PCR amplification. The disclosed probes and PCR primers are directed to the pil E gene, which encodes the predominant surface antigen of GC.

Stary et al., *J. Clin. Microbiol.* 35, 239 (1997), discloses a method for identifying GC based on ligase chain reaction (LCR) amplification of a target sequence within the opa I gene. Buimer et al., *J. Clin. Microbiol.* 34, 2395 (1996), concerns a diagnostic test for simultaneously detecting both GC and *Chlamydia trachomatis* by LCR amplification using one set of primers directed against the opa genes of GC and a second set of primers targeting the *C. trachomatis* endogenous plasmid. Crotchfelt et al., *J. Clin. Microbiol.* 35, 1536 (1997) and Iwen et al., *J. Clin. Microbiol.* 33, 2587 (1995), provide assays for simultaneous detection of GC and C trachomatis by PCR coamplification and rRNA hybridization, respectively.

Notwithstanding the investigations described above, there remains a need in the art for rapid, accurate and sensitive methods for the identification of GC.

SUMMARY OF THE INVENTION

The present invention provides a newly-identified region of the *Neisseria gonorrhoeae* ("GC") genome that can be used to detect *N. gonorrhoeae* nucleic acids by hybridization or amplification assays. Nucleic acid probes and amplification primers have been developed that result in the species-specific identification of GC without detectable cross-reactivity with non-GC species.

A first aspect of the present invention is a method for species-specific detection of *Neisseria gonorrhoeae* nucleic acids comprising the steps of: (a) hybridizing an oligonucleotide probe to *Neisseria gonorrhoeae* nucleic acids, the probe consisting of at least 10 consecutive nucleotides of a *Neisseria gonorrhoeae* GC3 sequence; and then (b) detecting hybridization between the oligonucleotide probe and the *Neisseria gonorrhoeae* nucleic acids.

As a second aspect, the present invention provides a method for species-specific detection of *Neisseria gonorrhoeae* nucleic acids comprising the steps of: (a) hybridizing to *Neisseria gonorrhoeae* nucleic acids at least one amplification primer comprising a target binding sequence, the target binding sequence consisting of at least 10 consecutive nucleotides of a *Neisseria gonorrhoeae* GC3 sequence; and (b) amplifying the *Neisseria gonorrhoeae* nucleic acids with the at least one amplification primer; and then (c) detecting the amplified *Neisseria gonorrhoeae* nucleic acids. In preferred embodiments, the amplification primer contains sequences for amplification of the target nucleic acids. Also preferred, are methods in which the target nucleic acids are amplified by thermophilic strand displacement amplification (tSDA).

As a third aspect, the present invention provides a method for species-specific detection of *Neisseria gonorrhoeae* nucleic acids comprising the steps of: (a) hybridizing to *Neisseria gonorrhoeae* nucleic acids a first and a second amplification primer, each of the first and second amplification primers comprising a target binding sequence and a sequence for amplification of the target nucleic acids, wherein the target binding sequence of the first amplification primer is selected from the group consisting of the target binding sequences of SEQ ID NO:20, SEQ ID NO:21, and SEQ ID NO:22, and wherein the target binding sequence of the second amplification primer is selected from the group consisting of the target binding sequences of SEQ ID NO:23, SEQ ID NO:24, SEQ ID NO:25, and SEQ ID NO:26; and (b) extending the hybridized first and second amplification primers on the *Neisseria gonorrhoeae* target nucleic acids, whereby the target nucleic acids are amplified; and then (c) detecting the amplified *Neisseria gonorrhoeae* nucleic acids.

A fourth aspect of the present invention is isolated DNA consisting of a *Neisseria gonorrhoeae* GC3 sequence. In preferred embodiments the GC3 sequence is selected from the group consisting of SEQ ID NO:2, SEQ ID NO:5, SEQ ID NO:6, SEQ ID NO:7, SEQ ID NO:8, SEQ ID NO:9, and SEQ ID NO:10. Further disclosed are oligonucleotide probes and amplification primers comprising a target binding sequence comprising at least 10 consecutive nucleotides of a GC3 sequence. Preferably, the oligonueleotide has a sequence selected from the group consisting of SEQ ID NO:3, SEQ ID NO:4, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, the target binding sequence of SEQ ID NO:20, the target binding sequence of SEQ ID NO:21, the target binding sequence of SEQ ID NO:22, the target binding sequence of SEQ ID NO:23, the target binding sequence of SEQ ID NO:24, the target binding sequence of SEQ ID NO:25, the target binding sequence of SEQ ID NO:26, SEQ ID NO:27, SEQ ID NO:28, SEQ ID NO:29, SEQ ID NO:30, SEQ ID NO:31, SEQ ID NO:32, and SEQ ID NO:33.

A fifth aspect of the present invention is a primer set for species-specific amplification of *Neisseria gonorrhoeae* nucleic acids comprising a first amplification primer comprising a target binding sequence consisting of at least 10 consecutive nucleotides of an isolated GC3 sequence. Preferably, the first amplification primer is selected from the group consisting of SEQ ID NO:3, SEQ ID NO:4, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, the target binding sequence of SEQ ID NO:20, the target binding sequence of SEQ ID NO:21, the target binding sequence of SEQ ID NO:22, the target binding sequence of SEQ ID NO:23, the target binding sequence of SEQ ID NO:24, the target binding sequence of SEQ ID NO:25, the target binding sequence of SEQ ID NO:26, SEQ ID NO:27, SEQ ID NO:28, SEQ ID NO:29, SEQ ID NO:30, SEQ ID NO:31, SEQ ID NO:32, and SEQ ID NO:33. In alternate embodiments, the first amplification primer further comprises a sequence for amplification of the target nucleic acids. According to this embodiment, the first amplification primer is preferably selected from the group consisting of SEQ ID NO:20, SEQ ID NO:21, SEQ ID NO:22, SEQ ID NO:23, SEQ ID NO:24, SEQ ID NO:25, and SEQ ID NO:26. Further disclosed are kits for species-specific detection of *Neisseria gonorrhoeae* nucleic acids comprising the inventive oligonucleotide probes and primers.

A sixth aspect of the present invention is a primer set for species-specific amplification of *Neisseria gonorrhoeae* nucleic acids comprising a first amplification primer consisting of SEQ ID NO:22, a second amplification primer consisting of SEQ ID NO:24, a first bumper primer consisting of SEQ ID NO:27, and a second bumper primer consisting of SEQ ID NO:28.

These and other aspects of the present invention are described in more detail in the description of the invention set forth below.

BRIEF DESCRIPTION OF THE DRAWINGS

FIG. 1 represents one strand of the GC3 DNA sequence (SEQ ID NO:2) from GC strain ATCC 19424. The stop codon (TAG) at nucleotides 237–239 is underlined.

FIG. 2 shows the alignment of the GC3 sequences from six GC strains (ATCC 19424—SEQ ID NO:2; ATCC 35541—SEQ ID NO:6; ATCC 43069 —SEQ ID NO:7; ATCC 43070—SEQ ID NO:8; BDMS 2900—SEQ ID NO:9; and CDC 111—SEQ ID NO:10). A consensus GC3 sequence (SEQ ID NO:5) was derived from the six individual sequences and is shown at the top of the alignment.

FIG. 3B shows the nucleotide sequences (SEQ ID NO:11 to SEQ ID NO:19) of the 9 PCR primers used in the PCR mapping studies. There were 4 left-hand and 5 right-hand primers evaluated.

FIG. 4A presents the tSDA primers, bumpers, and detectors of the GC3 tSDA system. The sequences of the GC3 tSDA amplification primers (SEQ ID NO:20 to SEQ ID NO:26), bumpers (SEQ ID NO 27 to SEQ ID NO:29), and detectors SEQ ID NO:30 to SEQ ID NO:33) are shown. The target binding sequences and the Bso B1 sites of the amplification primers are indicated by underlining and italics, respectively.

Figure 3A:
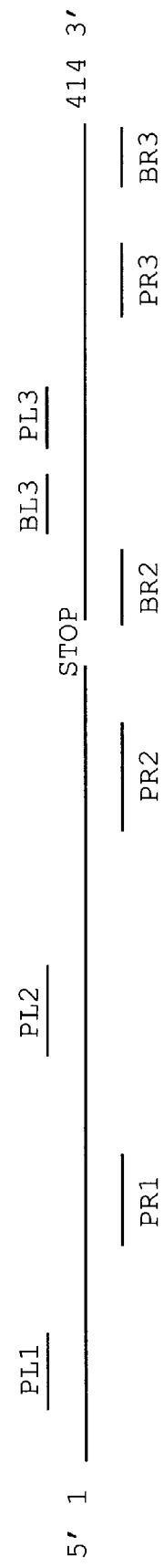
FIG. 3A presents the PCR mapping studies of the GC3 fragment. The relative positions (not to scale) of the target sequences of the 9 PCR primers on the GC3 fragment are shown. The "L" primers (above the GC3 fragment) are left primers, with the 5' to 3' direction from left to right. Similarly, the "R" primers (below the GC3 fragment) are "right" primers, with the 5' to 3' direction from right to left.

FIG. 4B shows the GC3 tSDA system chosen for further study. This set of amplification primers and bumpers targets a region spanning the stop codon and results in a 62 bp amplification product.

DETAILED DESCRIPTION OF THE INVENTION

Nucleotide sequences are presented herein by single strand only in the 5' to 3' direction, from left to right. Nucleotides are represented herein in the manner recommended by the IUPAC-IUB Biochemical Nomenclature Commission, in accordance with 37 C.F.R. § 1.822 and established usage.

The production and use of cloned genes, recombinant DNA, vectors, transformed host cells, selectable markers, proteins, and protein fragments by genetic engineering are well-known to those skilled in the art. See, e.g., U.S. Pat. No. 4,761,371 to Bell et al. at Col. 6 line 3 to Col. 9 line 65; U.S. Pat. No. 4,877,729 to Clark et al. at Col. 4 line 38 to Col. 7 line 6; U.S. Pat. No. 4,912,038 to Schilling at Col. 3 line 26 to Col. 14 line 12; and U.S. Pat. No. 4,879,224 to Wallner at Col. 6 line 8 to Col. 8 line 59.

Disclosed herein is a newly-identified region of the *Neisseria gonorrhoeae* ("GC") genomic DNA, which has been designated "GC3". The GC3 sequence exhibits a high degree of homology across GC strains. The GC3 sequences disclosed herein find use in methods of detecting and diagnosing GC. For example, these sequences can be used to design hybridization probes for use in conventional Southern or dot blot hybridizations, or to design amplification primers for use in nucleic acid amplification procedures, such as Polymerase Chain Reaction (PCR), Ligase Chain Reaction (LCR), Strand Displacement Amplification (SDA), or thermophilic Strand Displacement Amplification (tSDA). Also disclosed herein are oligonucleotides, methods and kits for detection, preferably species-specific detection, of GC.

The GC3 sequences disclosed herein include the sequences given as SEQ ID NO:2, SEQ ID NO:6, SEQ ID NO:7, SEQ ID NO:8, SEQ ID NO:9, and SEQ ID NO:10, and the complementary sequences thereof. As used herein, the term "GC3 sequences" also encompasses GC3 sequences from strains of GC other than those specifically disclosed herein. Alternatively stated, GC3 sequences of the present invention include the amplification products (i. e., amplicons) resulting from amplification of GC nucleic acids with GC3 specific amplification primers, such as SEQ ID NO:3 and SEQ ID NO:4. GC3 sequences from strains of GC other than those specifically disclosed herein will generally be at least about 75% homologous (and more preferably 80%, 85%, 90% or even 95% homologous) to a continuous segment of DNA found within the GC3 sequences given herein as SEQ ID NO:2, SEQ ID NO:6, SEQ ID NO:7, SEQ ID NO:8, SEQ ID NO:9, and SEQ ID NO:10, and the complementary sequences thereof, and will be able to hybridize to GC nucleic acids under conditions of high stringency, as defined below.

The GC3 sequences of the present invention include sequences that hybridize under conditions of high stringency to GC nucleic acids and are substantially homologous to the GC3 sequences specifically disclosed herein, and particularly the GC3 sequences disclosed herein as SEQ ID NO:2, SEQ ID NO:6, SEQ ID NO:7, SEQ ID NO:8, SEQ ID NO:9, and SEQ ID NO:10, and the complementary sequences thereof. This definition is intended to encompass natural allelic variations in the GC3 sequence. As used herein, nucleotide sequences that are "substantially homologous" are at least 75%, and more preferably are 80%, 90% or even 95% homologous.

High stringency hybridization conditions that will permit homologous DNA sequences to hybridize to a DNA sequence as given herein are well known in the art. For example, hybridization of such sequences to DNA disclosed herein may be carried out in 25% formamide, 5× SSC, 5× Denhardt's solution, with 100 μg/ml of single stranded DNA, and 5% dextran sulfate at 42° C., with wash conditions of 25% formamide, 5× SSC, 0.1% SDS at 42° C. for 15 minutes, to allow hybridization of sequences of about 60% homology. More stringent conditions are represented by a wash stringency of 0.3 M NaCl, 0.03 M sodium citrate, 0.1% SDS at 60° C., or even 70° C. See Sambrook et al., MOLECULAR CLONING, A LABORATORY MANUAL (2d ed. 1989), herein incorporated by reference in its entirety. In general, GC3 sequences which hybridize to the GC3 sequences disclosed herein will be at least 75%, 80%, 85%, 90% or even 95% homologous or more with the GC3 sequences disclosed herein.

Oligonucleotide hybridization probes are also aspects of the present invention. As used herein, the term "probe" indicates an oligonucleotide that hybridizes to a target sequence, typically to facilitate its detection. As used herein, a "target sequence" refers to a nucleic acid sequence to which the probe specifically binds. Unlike a primer, a probe is not extended by a polymerase. The probe is often linked (directly or indirectly) to a detectable label to facilitate detection or capture when hybridized to the target sequence.

The probes disclosed herein hybridize to GC3 nucleic acids. Typically, the probes of the present invention will hybridize to consecutive nucleotides of the GC3 sequences disclosed herein under stringent conditions, as defined above. Alternatively stated, probes of the present invention will be at least 75%, 80%, 85%, 90% or even 95% homologous or more with consecutive nucleotides within the GC3 sequences disclosed herein, in particular SEQ ID NO:2, SEQ ID NO:6, SEQ ID NO:7, SEQ ID NO:8, SEQ ID NO:9, and SEQ ID NO:10, and the complements thereof. In particular embodiments of the invention, the probes have nucleotide sequences as given herein as SEQ ID NO:3, SEQ ID NO:4, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, the target binding sequence of SEQ ID NO:20, the target binding sequence of SEQ ID NO:21, the target binding sequence of SEQ ID NO:22, the target binding sequence of SEQ ID NO:23, the target binding sequence of SEQ ID NO:24, the target binding sequence of SEQ ID NO:25, the target binding sequence of SEQ ID NO:26, SEQ ID NO:27, SEQ ID NO:28, SEQ ID NO:29, SEQ ID NO:30, SEQ ID NO:31, SEQ ID NO:32, and SEQ ID NO:33, and complementary sequences thereof.

As nucleic acids do not require complete homology to hybridize, it will be apparent to those skilled in the art that the probe sequences specifically disclosed herein may be modified so as to be substantially homologous to the probe sequences disclosed herein without loss of utility as GC probes. It is well-known in the art that hybridization of homologous and partially homologous nucleic acid sequences may be accomplished by adjusting the hybridization conditions to increase or decrease the stringency (i.e., adjusting the hybridization temperature or salt content of the buffer).

Hybridization probes can be of any suitable length. There is no particular lower or upper limits to the length of the probe, as long as the probe hybridizes to the target GC3 nucleic acids and functions effectively as a probe (e.g., facilitates detection). In one preferred embodiment of the invention the probe comprises at least 10 consecutive nucleotides of a GC3 sequence, as defined above. The probes of the present invention can be at short as 50, 40, 30, 20, 15, or 10 nucleotides, or shorter. Likewise, the probes can be as long as 20, 40, 50, 60, 75, 100 or 200 nucleotides, or longer. The maximum length of the probe is the length of the particular GC3 sequence selected. For example, a probe derived from the GC strain ATTC 19424 sequence (see FIG. 1; SEQ ID NO:2) can be as long as 415 nucleotides.

In a preferred embodiment, the probe is species-specific, meaning that under stringent conditions (as defined above, e.g., a wash stringency of 0.3 M NaCl, 0.03 M sodium citrate, 0.1% SDS at 60° C.) it hybridizes only to nucleic acids from GC and does not hybridize to nucleic acids from any non-GC species, or does so to a negligible extent, such that there is only insignificant hybridization or detection of non-GC nucleic acids. Alternately stated, a GC-specific probe does not hybridize to or detect non-GC nucleic acids (or does so to only an insignificant extent) under the same conditions in which the probe does hybridize to and detect GC nucleic acids.

Another aspect of the present invention is a method for detecting GC using a GC3 probe, as defined above. According to this embodiment of the invention, a nucleic acid probe is hybridized to GC nucleic acids, and the hybridization between the probe and the GC nucleic acids is then detected. A preferred embodiment of the invention is a species-specific (as defined above) method of detecting GC using a hybridization probe.

Hybridization can be carried out using any suitable technique known in the art. Typically, hybridizations will be performed under conditions of high stringency. It will be apparent to those skilled in the art that hybridization conditions can be altered to increase or decrease the degree of hybridization, the level of specificity of the hybridization, and the background level of non-specific binding (i.e., by altering hybridization or wash salt concentrations or temperatures).

Similarly, detection of hybridization between the probe and the GC nucleic acids can be carried out by any method known in the art. The probe may contain a detectable label that will indicate hybridization between the labeled probe and the GC nucleic acids. The detectable label of the probe is a moiety that can be detected either directly or indirectly. For direct detection of the label, probes may be tagged with a radioisotope and detected by autoradiography. Alternatively, the probe may be tagged with a fluorescent moiety and detected by fluorescence, as is known in the art. As a further alternative, the probe may be indirectly detected by tagging with a label that requires additional reagents to render it detectable. Illustrative methods of indirect labeling include those utilizing chemiluminescence agents, enzymes that produce visible reaction products, and ligands (e.g., haptens, antibodies or antigens) that may be detected by binding to labeled specific binding partners (e.g., hapten binding to a labeled antibody). Ligand labels are also useful for solid phase capture of the oligonucleotide probe (i.e., capture probes). Exemplary labels include biotin (detectable by binding to labeled avidin or streptavidin) and enzymes, such as horseradish peroxidase or alkaline phosphatase (detectable by addition of enzyme substrates to produce a colored reaction product). Methods of labeling oligonucleotides are well known in the art.

GC3 amplification primers are also encompassed by the present invention. An amplification primer is an oligonucleotide useful for amplification of a target sequence by extension of the oligonucleotide after hybridization to the target sequence, or by ligation of multiple oligonucleotides that are adjacent when hybridized to the target sequence. The oligonucleotide primers of the present invention are preferably used to detect GC by extension of the hybridized oligonucleotide primer.

Copies of the target sequence which are generated during the amplification reaction are referred to as "amplification products", "amplimers", or "amplicons". An extension product refers to the copy of a target sequence produced by hybridization of a primer and extension of the primer by polymerase using the target sequence as a template.

As used herein, the "target sequence" of an amplification primer refers to a GC nucleic acid sequence to which the "target binding sequence" of the amplification primer specifically binds and amplifies. These include the original nucleic acid sequence to be amplified and its complementary second strand as well as either strand of a copy of the original target sequence generated during the amplification reaction. The portion of the primer that hybridizes to the target sequence (i.e., target binding sequence or annealing region) may also be used as a hybridization probe for detection of target GC nucleic acids in various nucleic acid hybridization methods, as described in more detail above.

Thus, it will be apparent to those skilled in the art that primers and probes of the present invention may be structurally similar or identical. The terms "primer" and "probe" refer to the function of the oligonucleotide. An oligonucleotide may function as a probe if it is hybridized to a target sequence to capture or detect the target sequence. Alternately, the same oligonucleotide may function as a primer if it is used to amplify the target, as described below.

Suitable bases for preparing the oligonucleotide probes or amplification primers of the present invention may be selected from naturally occurring nucleotide bases such as adenine, cytosine, guanine, uracil, and thymine; and non-naturally occurring or "synthetic" nucleotide bases such as 8-oxo-guanine, 6-mercaptoguanine, 4-acetylcytidine, 5-(carboxyhydroxyethyl)uridine, 2'-O-methylcytidine, 5-carboxymethylamino-methyl-2-thioridine, 5-carboxymethylaminomethyluridine, dihydrouridine, 2'-O-methylpseudouridine, β,D-galactosylqueosine,2'-O-methylguanosine, inosine, $N^6$-isopentenyladenosine, 1-methyladenosine, 1-methylpseudouridine, 1-methylguanosine, 1-methylinosine,2,2-dimethylguanosine, 2-methyladenosine, 2-methylguanosine, 3-methylcytidine, 5-methylcytidine, $N^6$-methyladenosine, 7-methylguanosine, 5-methylaminomethyluridine, 5-methoxyaminomethyl-2-thiouridine,β,D-mannosylqueosine, 5-methoxycarbonylmethyluridine,5-methoxyuridine, 2-methylthio-$N^6$-isopentenyladenosine,N-((9-β-D-ribofuranosyl-2-methylthiopurine-6-yl)carbamoyl) threonine,N-((9-β-D-ribofuranosylpurine-6-yl)N-methylcarbamoyl)threonine,uridine-5-oxyacetic acid methylester, uridine-5-oxyaceticacid, wybutoxosine, pseudouridine, queosine, 2-thiocytidine, 5-methyl-2-thiouridine, 2-thiouridine, 2-thiouridine, 5-methyluridine, N-((9-β-D-ribofuranosylpurine-6-yl)carbamoyl)threonine,2'-O-methyl-5-methyluridine,2'-O-methyluridine, wybutosine, and 3-(3-amino-3-carboxypropyl)uridine.

Likewise, chemical analogs of oligonucleotides in which the phosphodiester bonds have been modified (e.g., to the methylphosphonate, the phosphotriester, the phosphorothioate, the phosphorodithioate, or the phosphoramidate) may also be employed. Protection from degradation can be achieved by use of a "3'-end cap" strategy by which nuclease-resistant linkages are substituted for phosphodiester linkages at the 3' end of the oligonucleotide. See Tidd and Warenius, *Br. J Cancer* 60, 343 (1989); Shaw et al., *Nucleic Acids Res.* 19, 747 (1991). Phosphoramidates, phosphorothioates, and methylphosphonate linkages all function adequately in this manner. More extensive modification of the phosphodiester backbone has been shown to impart stability and may allow for enhanced affinity and increased cellular permeation of oligonucleotides. See Milligan, et al., *J. Med Chem.* 36, 1923 (1993). Many different chemical strategies have been employed to replace the entire phosphodiester backbone with novel linkages. Id. Backbone analogues include phosphorothioate, phosphorodithioate, methylphosphonate, phosphoramidate, boranophosphate, phosphotriester, formacetal, 3'-thioformacetal, 5'-thioformacetal, 5'-thioether, carbonate, 5'-N-carbamate, sulfate, sulfonate, sulfamate, sulfonamide, sulfone, sulfite, sulfoxide, sulfide, hydroxylamine, methylene(methylimino) (MMI) or methyleneoxy (methylimino) (MOMI) linkages. Phosphorothioate and methylphosphonate-modified oligonucleotides are particularly preferred due to their availability through automated oligonucleotide synthesis. Id.

The oligonucleotide may also be a "peptide nucleic acid" such as described in Nielsen et al., *Science* 254, 1497 (1991). The only requirement is that the oligonucleotide probe should possess a sequence at least a portion of which is capable of binding to a portion of the sequence of a target DNA molecule.

The amplification primers disclosed herein hybridize to and amplify GC3 nucleic acids. When a set of two or more amplification primers is used to amplify GC3 nucleic acids, it is preferred that the set of amplification primers is contained in a common aqueous solution. Typically, amplification primers will hybridize to consecutive nucleotides of the GC3 sequences disclosed herein under stringent conditions, as defined above. Alternatively stated, primers of the present invention will be at least 75%, 80%, 85%, 90% or even 95% homologous or more with consecutive nucleotides within the GC3 sequences disclosed herein, in particular SEQ ID NO:2, SEQ ID NO:6, SEQ ID NO:7, SEQ ID NO:8, SEQ ID NO:9, and SEQ ID NO:10, and complements thereof.

Amplification primers can be of any suitable length. There is no particular lower or upper limits to the length of the primer, so long as the primer hybridizes to the target GC3 DNA and functions effectively as an amplification primer. In one preferred embodiment of the invention the primers comprise at least 10 consecutive nucleotides of a GC3 sequence, as defined above. The primers can be as short as 50, 40, 30, 20, 15, or 10 nucleotides, or shorter. Likewise, the primers can be as long as 20, 40, 50, 60, 75, 100 or 200 nucleotides, or longer.

In a preferred embodiment of the invention, the amplification primer is species-specific, meaning that under stringent conditions (as defined above), the amplification primer hybridizes to, amplifies, and detects only GC nucleic acids, and does not hybridize to, amplify, and detect nucleic acids from any non-GC species, or does so to a negligible extent, such that there is only insignificant hybridization, amplification and detection of non-GC nucleic acids. Alternately stated, a GC-specific amplification primer does not hybridize to, amplify, and detect non-GC nucleic acids (or does so to only an insignificant extent) under the same conditions in which the amplification primer does hybridize to, amplify, and detect GC nucleic acids.

In particular embodiments of the present invention, the amplification primer or its target binding sequence has a sequence as given by SEQ ID NO:3, SEQ ID NO:4, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, the target binding sequence of SEQ ID NO:20, the target binding sequence of SEQ ID NO:21, the target binding sequence of SEQ ID NO:22, the target binding sequence of SEQ ID NO:23, the target binding sequence of SEQ ID NO:24, the target binding sequence of SEQ ID NO:25, the target binding sequence of SEQ ID NO:26, SEQ ID NO:27, SEQ ID NO:28, SEQ ID NO:29, SEQ ID NO:30, SEQ ID NO:31, SEQ ID NO:32, and SEQ ID NO:33, and complementary sequences thereof. Alternatively, the amplification primer has a sequence as given by SEQ ID NO:20, SEQ ID NO:21, SEQ ID NO:22, SEQ ID NO:23, SEQ ID NO:24, SEQ ID NO:25 or SEQ ID NO:26, preferably, SEQ ID NO:22 or SEQ ID NO:24, or complementary sequences thereof.

In other preferred embodiments, the amplification primers are selected so that one primer targets 5' of the GC3 stop codon (e.g., the stop codon beginning at nucleotide 237 of SEQ ID NO:2) and a second primer targets 3' of the stop codon, and in the case of doubled-stranded DNA, on the complementary strand to the strand to which the first amplification primer hybridizes. According to this embodiment, the amplification primers will amplify across the stop codon, and the amplification product will include the stop codon. Preferably, one amplification primer has a sequence given as SEQ ID NO:3, SEQ ID NO:11, or SEQ ID NO:12, and the second amplification primer has a sequence given as SEQ ID NO:4, SEQ ID NO:17, SEQ ID NO:18, or SEQ ID NO:19. Also preferred are embodiments in which the first amplification primer has a sequence given as SEQ ID NO:15 or SEQ ID NO:16, and the second amplification primer has a sequence given as SEQ ID NO:13 or SEQ ID NO:14. More preferably, the first and second amplification primers have sequences given as SEQ ID NO:3 and SEQ ID NO:4, SEQ ID NO:11 and SEQ ID NO:18, SEQ ID NO:11 and SEQ ID NO:19, or SEQ ID NO:18 and SEQ ID 12, respectively.

As nucleic acids do not require complete homology to hybridize, it will be apparent to those skilled in the art that the primer sequences specifically disclosed herein may be modified so as to be substantially homologous to the primer sequences disclosed herein without loss of utility as GC amplification primers. It is well-known in the art that hybridization of homologous and partially homologous nucleic acid sequences may be accomplished by adjusting the hybridization conditions to increase or decrease the stringency (i.e., adjusting the hybridization temperature or salt content of the buffer).

The inventive amplification primers disclosed herein can be used in any method of nucleic acid amplification known in the art. Such methods include but are not limited to Polymerase Chain Reaction (PCR; described in U.S. Pat. Nos. 4,683,195, 4,683,202, 4,800,159, 4,965,188), Strand Displacement Amplification (SDA; described by Walker et al., *Proc. Nat. Acad. Sci. USA* 89, 392 (1992), herein incorporated by reference in its entirety; Walker et al., *Nucl. Acids Res.* 20, 1691 (1992), herein incorporated by reference in its entirety; U.S. Pat. No. 5,270,184), thermophilic Strand Displacement Amplification (tSDA; U.S. Pat. No. 5,648,211 and European Patent Application No. EP 0684315 to Frasier et al.), Self-Sustained Sequence Replication (3SR; J. C. Guatelli et al., *Proc Natl. Acad. Sci. USA* 87, 1874(1990)), Nucleic Acid Sequence-Based Amplification (NASBA; U.S. Pat. No. 5,130,238 to Cangene), the Qβ replicase system (P. Lizardi et al., *BioTechnology* 6, 1197 (1988)), and transcription based amplification (D. Y. Kwoh et al., *Proc. Natl. Acad. Sci. USA* 86, 1173 (1989)). Preferably, the amplification primers of the present invention are used to carry out SDA or tSDA, with tSDA being more preferred.

For amplification by tSDA (or SDA), the oligonucleotide primers are preferably selected such that the GC content is low, preferably less than 70% of the total nucleotide composition of the probe. Similarly, for tSDA the target sequence preferably has a low GC content to minimize secondary structure. An amplification primer for use in tSDA comprises a target binding sequence, a recognition site for a restriction endonuclease, and a tail. The target binding sequence is at the 3' end of the tSDA amplification primer. It hybridizes to the 3' end of the target sequence. The target binding sequence confers hybridization specificity on the amplification primer. A recognition site for a restriction endonuclease is 5' of the target binding sequence. The restriction endonuclease is one that will nick one strand of a DNA complex when the recognition site is hemimodified, as described by Walker et al. (*Proc. Nat'l Acad. Sci. USA* 89, 392 (1992); *Nucl. Acids. Res.* 20, 1691 (1992); both publications are herein incorporated by reference in their entirety). The tail of the amplification primer is comprised of the nucleotides 5' of the restriction endonuclease recognition site. The length and sequence of the tail are generally not critical. The tail functions as a polymerase repriming site when the remainder of the amplification primer is nicked and displaced during tSDA.

As used herein, a "bumper primer" or "external primer" is a primer used to displace primer extension products. The bumper primer hybridizes to a target sequence upstream of the amplification primer target sequence such that extension of the bumper primer displaces the downstream amplification primer and its extension product. Generally, it will not be necessary that the bumper primers used in SDA and tSDA reactions be GC-specific. The bumper primers are only required to hybridize to their targets upstream from the amplification primers, so that when the bumper primers are extended they will displace the amplification primer and its extension product. The sequence of the bumper primers is therefore generally not critical, and may be derived from any upstream target sequence that is sufficiently close to the binding site of the amplification primer to allow displacement of the amplification primer extension product upon extension of the bumper primer. Occasional mismatches with the target in the bumper primer sequence or some cross-hybridization with non-target sequences do not generally have a negative effect on amplification efficiency as long as the bumper primer still hybridizes to the specific target sequence. Extension of bumper primers is one method for displacing the extension products of amplification primers, but heating is also suitable. In one embodiment of the invention, bumpers comprise at least 10 consecutive nucleotides of a GC3 sequence, as defined above. In preferred embodiments, one or more of the bumper primers have sequences as given herein by SEQ ID NO:27, SEQ ID NO:28, and SEQ ID NO:29, preferably SEQ ID NO:27 and SEQ ID NO:28. Bumper primers may also be used as the target binding sequence of an amplification primer or as a hybridization probe, each as defined above.

For amplification methods that do not require specialized sequences at the ends of the target (e.g., PCR and LCR), the amplification primer typically consists essentially of only the target binding sequence. In the case of amplification methods that require primers containing specialized sequences in addition to the target-binding sequence, the specialized sequence may be linked to the target binding sequence using routine methods for preparation of oligonucleotides without altering the hybridization specificity of the target binding sequence. Illustrative examples of amplification methods requiring specialized primer sequences for amplification include: SDA and tSDA, 3SR, NASBA, and transcription based amplification. These specialized sequences do not hybridize to the target nucleic acids, but instead perform a separate function, which is required for amplification (e.g., the restriction enzyme site and primer tail in SDA and tSDA primers).

Another aspect of the present invention is a method of detecting GC by hybridizing at least one amplification primer comprising a target binding sequence to GC nucleic acids, amplifying the GC nucleic acids, and then detecting the amplified GC nucleic acids. Preferred are species-specific (as defined above) methods of detecting GC using an amplification primer(s). The amplification primer(s) hybridizes to, amplifies, and detects nucleic acids from the GC3 sequence. Typically, the target sequence of the amplification primer will be double-stranded DNA of the GC3 sequence of the GC genome.

Preferably, the inventive methods disclosed herein employ a set of two or more amplification primers to amplify the GC target sequences. Alternately, a single amplification primer can be used to carry out the present invention. A "primer set" comprises two or more primers that are designed or adapted to function together to 15 amplify the target sequence. A primer set may only include amplification primers or it may also encompass bumper primers (e.g., for SDA and tSDA reactions). As a further alternative, a primer set may contain one or more additional or alternate primers for carrying out the inventive methods. Preferably, the primer set includes two amplification primers for PCR or two amplification primers and two bumper primers for SDA/tSDA. Amplification primers for use in carrying out the methods disclosed herein are as described hereinabove.

In one preferred embodiment of the invention, the amplification primers are hybridized to the GC nucleic acids and extended. Amplification methods involving extension reactions include, but are not limited to, SDA and tSDA. Any amplification protocol which relies on cyclic, specific hybridization of primers to the target nucleic acid may be used, such as, PCR, SDA, tSDA, 3SR, the Qβ replicase system, or transcription based amplification. Amplification by SDA and tSDA is preferred, with tSDA being more preferred. The tSDA reactions can be carried out as described by U.S. Pat. No. 5,648,21 1 and European Application No. EP 0 684 315 to Frasier et al. Briefly, amplification by tSDA is based upon 1) the ability of a restriction endonuclease to nick the unmodified strand of a hemiphosphorothioate form of its double-stranded recognition site, and 2) the ability of certain polymerases to initiate replication at the nick and displace the downstream non-template strand. In tSDA reactions, the extension of primers, nicking of a hemi-modified restriction endonuclease recognition site, displacement of single-stranded extension products, annealing of primers to the extension products and subsequent extension of the primers occurs concurrently in the reaction mix. This is in contrast to PCR, in which the steps of the reaction occur in discrete phases or cycles as a result of the temperature cycling characteristics of the reaction.

Amplification reactions employing the primers of the present invention may incorporate thymine as disclosed by Walker et al. (*Proc. Nat'l Acad. Sci. USA* 89, 392 (1992);

Nucl. Acids. Res. 20, 1691 (1992); both publications are herein incorporated by reference in their entirety), or they may wholly or partially substitute 2'-deoxyuridine 5'-triphosphate for TTP in the reaction to reduce cross-contamination with amplification products carried over from previous amplification reactions in reagents, pipetting devices and laboratory surfaces, for example, as is taught in European Patent No. 0 624 643. Deoxyuridine (dU) is incorporated into amplification products and can be excised by treatment with uracil DNA glycosylase (UDG). These a basic sites render any contaminating amplification product unamplifiable in subsequent amplification reactions. UDG may be inactivated by UDG inhibitor prior to performing the subsequent amplification to prevent excision of dU in newly-formed amplification products.

In another preferred embodiment of the invention, amplification is carried out by hybridizing two or more amplification primers to the GC nucleic acids, such that the primers are adjacent to each other when hybridized to their respective target sequences, and then ligating the hybridized amplification primers to produce a longer amplification product.

The presence of GC or GC nucleic acids is detected by determining the presence of the amplified GC nucleic acids. Amplification products can be detected by hybridization to a labeled probe, as described above. When a probe is used to detect amplification, the probe is typically selected to hybridize to a sequence that lies between the amplification primers (i.e., an internal probe). When amplification is performed by LCR, a probe that overlaps both primers and does not detect unligated primers may be used. Alternatively, amplification products may be detected by their characteristic size, for example by electrophoresis followed by ethidium bromide staining to visualize the nucleic acids species. This is the preferred method of detecting amplification products for LCR methods. In a further alternative, a labeled amplification primer is used. In a still further alternative, a labeled amplification primer/internal probe is extended on the target sequence (a detector primer) for detection of amplification products as described by Walker et al. *Proc. Nat'l Acad. Sci. USA* 89, 392 (1992); *Nucl. Acids. Res.* 20, 1691 (1992); both publications are herein incorporated by reference in their entirety.

Examples of specific detection methods that may be employed to detect amplification products include a chemiluminescent method in which amplified products are detected using a biotinylated capture probe and an enzyme-conjugated detector probe as described in U.S. Pat. No. 5,470,723. After hybridization of these two probes to different sites of the assay region of the target sequence (i.e., between the binding sites of the two amplification primers), the complex is captured on a streptavidin-coated microtiter plate, and the chemiluminescent signal is developed and read in a luminometer. As a further alternative method, a signal primer as described in European Patent No. 0 678 582 is included in the amplification reaction to facilitate detection of the amplification product. According to this embodiment, labeled secondary amplification products are generated during amplification in a target amplification-dependent manner and may be detected as an indication of target amplification by means of the associated label.

The present invention also provides kits for detecting GC nucleic acids comprising a nucleic acid probe or amplification primer, preferably a pair of amplification primers or a primer set, each as described hereinabove. Species-specific methods, probes, amplification primers, and primer sets for detecting GC, as described hereinabove, are preferred. The kit may optionally contain means for detecting the GC nucleic acids using an oligonucleotide probe or amplification primer, as described hereinabove. Preferably, the oligonucleotide probe or amplification primer comprises at least 10 consecutive nucleotides of a GC3 sequence. In an alternate embodiment, the amplification primer contains a sequence for amplification of a target nucleic acid in addition to a target binding sequence, each as described hereinabove. The kit may further include other components and reagents for performing the hybridization or amplification method (e.g., Southern hybridization, dot blot hybridization, PCR, SDA, etc., and the like). As an illustrative example, such a kit may contain at least one amplification primer according to the present invention. For detection by hybridization, a hybridization solution such as 25% formamide, 5× SSC, 5× Denhardt's solution, 100 μg/ml of single stranded DNA, and 5% dextran sulfate, or other reagents known to be useful for probe hybridization may also be included. See Sambrook et al., MOLECULAR CLONING, A LABORATORY MANUAL (2d ed. 1989); herein incorporated by reference in its entirety. Alternatively, reagents appropriate for use with one of the known nucleic acid amplification methods may be included with GC3 amplification primers. The components of the kit are packaged together in a common container, typically including written instructions for performing selected specific embodiments of the methods disclosed herein. Components for detection methods, as described hereinabove, may optionally be included in the kit, for example, a second probe, and/or reagents and means for performing label detection (e.g., radiolabel, enzyme substrates, antibodies, etc., and the like).

The methods, probes, amplification primers, and kits disclosed herein can be used to detect GC in any sample suspected of containing GC. The samples may comprise isolated nucleic acids, isolated microorganisms, or they may be clinical samples. Typically, clinical samples are in the form of a biological fluid or tissue (e.g., sputum, soft tissues, urine, discharge). The samples may also be obtained by swabs, for example, pharyngeal, conjunctival, urethral, vaginal, cervical, genital or anorectal swabs.

It is common in the art to screen for *N. gonorrhoeae* in conjunction with one or more other sexually transmitted diseases, in particular, *Chlamydia trachomatis*. The diagnostic probes, amplification primers, methods, and kits disclosed herein for detecting GC may be used alone or together with diagnostic means and techniques for other microorganisms, preferably other sexually transmitted pathogens, more preferably *Chlamydia trachomatis*.

The following Examples are provided to illustrate the present invention and should not be construed as limiting thereof.

EXAMPLE 1

Identification of a *N. gonorrhoeae* Specific DNA Fragment (GC3)

Arbitrary primed polymerase chain reaction (AP-PCR) was used to create a differential display of amplification products from the genomic DNA of 2 *N. gonorrhoeae* ("GC") species and 2 non-GC species (Table 1). The primer for AP-PCR was as follows:

Primer CRL11: 5' CGG TTG CCT CCA TGC AGA T 3' (SEQ ID NO:1)

The conditions for the amplification reaction are given below.

PCR Reaction Conditions (50 μl):

10 mM Tris-HCl, pH 8.3 (at 25° C.)
50 mM KCl
1.5 mM MgCl$_2$
0.001% (w/v) gelatin
0.2 mM dNTPs
0.2 µM $^{32}$p labeled primer CRL 11 (SEQ ID NO:1)
100 ng genomic DNA as template
2.5 U Taq DNA polymerase Gold™ (Perkin-Elmer)

The primers were 5' radiolabeled ($^{32}$P) according to the manufacturer's instructions (Random Primed DNA labeling kit, Boehringer Mannheim). The AP-PCR was carried out in a Perkin-Elmer Cetus thermocycler (Model 480), using the amplification profile given below.

PCR Profile:
 95° C. 3 minutes Then change to:
 94° C. 2 minute
 64° C. 2 minutes
 72° C. 2 minutes
 15 Cycles Then change to:
 94° C. 2 minutes
 37° C. 2 minutes
 72° C. 2 minutes
 1 Cycle Then change to:
 94° C. 2 minutes
 60° C. 2 minutes
 72° C. 2 minutes
 35 Cycles Then change to:
 4° C. overnight Amplification products were isolated and visualized by electrophoresis through an 8% denaturing acrylamide gel (100 W) for 4 hours, followed by autoradiography (overnight exposure with Fuji medical X-Ray film). A unique band was identified that was present in both GC strains, but was absent in the non-GC species tested. This band was designated "GC3".

TABLE 1

Target Organisms for Arbitrary Primed Polymerase Chain Reaction

| Targets | ID# |
|---|---|
| Neisseria gonorrhoeae | ATCC 19424 |
| Neisseria gonorrhoeae | ATCC 35541 |
| Neisseria lactamica | ATCC 44418 |
| Neisseria meningitidis | ATCC 13077 |

EXAMPLE 2

Re-Amplification of the GC3 DNA Fragment by Arbitrary Primed Polymerase Chain Reaction (AP-PCR)

The GC3 band was excised from the gel, and the DNA was extracted by boiling the acrylamide gel slice in 100 µl of distilled sterile water for 15 minutes, followed by ethanol precipitation using glycogen as a carrier. The extracted DNA was used to re-amplify the GC3 band by AP-PCR using the CRL 11 primer (SEQ ID NO:1) from Example 1. The AP-PCR reaction conditions were as described in Example 1, with 5 µl of the extracted DNA used as template in place of the 100 ng of genomic DNA. The amplification profile was as given below.

PCR Profile:
 95° C. 2 minutes Then change to:
 94° C. 1 minute
 60° C. 2 minutes
 72° C. 2 minutes
 35 Cycles Then change to:
 4° C. overnight Amplification products were isolated and visualized as described in Example 1. A PCR product of approximately 450 bp (as expected) was visible, representing the GC3 fragment.

EXAMPLE 3

Cloning of the GC3 Fragment

The re-amplified GC3 fragment from Example 2 was cloned into the PCR TA II™ vector (Invitrogen; Carlsbad, Calif.) according to the manufacturer's instructions. Bacterial cells were transformed with the pTA II™-GC3 vector. The multiple cloning region of the pTA II™ vector has two Eco R1 sites flanking the insert, and the presence of the GC3 fragment in transformed bacterial colonies was confirmed by Eco R1 digestion. The restriction digestion released a DNA fragment of approximately 450 base pairs in length, corresponding to the GC3 fragment.

EXAMPLE 4

Sequencing of the GC3 Fragment

The GC3 DNA fragment cloned into the pTA II™ vector was sequenced using primers designed for the M13+ and M13- promoters located in the vector. The ABI PRISM Terminator cycle sequencing kit (Perkin-Elmer) was used to cycle sequence the GC3 DNA fragment in a Perkin-Elmer Cetus Thermocycler (model 480) following the manufacturers' protocols. The amplified products were purified and run on an Applied Biosystems 373 DNA Sequencer. The GC3 sequence (SEQ ID NO:2) from one GC strain (ATCC 19424) is shown in FIG. 1. The 5' region of the GC3 fragment has a 78 amino acid open reading frame and a stop codon beginning at position 237. The 3' region following the stop codon does not contain an open reading frame. No similar DNA sequence was found among over 600 sequence entries for Neisseria species in GenBank.

EXAMPLE 5

GC-Specific PCR Primers

Based on the sequence information obtained in Example 4, GC3 PCR primers were designed (shown below), to evaluate the species-specificity of the GC3 fragment. The primers were targeted to the 5' and 3' ends of the GC3 fragment.

Primer GC3-5': 5' CAT ACT GTA CCA TAG CGT T 3' (SEQ ID NO:3)

Primer GC3-3': 5' ATT CTG ACA TCC CAA GCT T 3' (SEQ ID NO:4)

Genomic DNA from 12 GC strains and 19 non-GC species were amplified using the GC3 primers. The PCR reaction conditions were as described in Example 1, with the exception that only 50 ng of template DNA was amplified. The amplification profile was as shown below.

PCR Profile:
 95° C. 3 minutes Then change to:
 94° C. 1 minute

60° C. 2 minutes
72° C. 2 minutes
35 Cycles Then change to:
4° C. overnight

The PCR amplification products were isolated and visualized by electrophoresis and autoradiography as described above in Example 1. The results are shown below in Table 2. All of the GC strains were successfully amplified by PCR using the GC3-specific PCR primers, while none of the non-GC species gave detectable amplification product. These results demonstrate that the GC3 fragment and GC3 PCR primers are species-specific for GC.

TABLE 2

Species-Specificity of GC3 PCR Primers

| Template DNA | ID# | Amplification |
|---|---|---|
| GC strains: | | |
| Neisseria gonorrhoeae | CDC 111 | + |
| Neisseria gonorrhoeae | BDMS 1632 | + |
| Neisseria gonorrhoeae | ATCC 19424 | + |
| Neisseria gonorrhoeae | BDMS 2900 | + |
| Neisseria gonorrhoeae | ATCC 25301 | + |
| Neisseria gonorrhoeae | ATCC 35541 | + |
| Neisseria gonorrhoeae | ATCC 35542 | + |
| Neisseria gonorrhoeae | ATCC 43069 | + |
| Neisseria gonorrhoeae | ATCC 43070 | + |
| Neisseria gonorrhoeae | BDMS 454 | + |
| Neisseria gonorrhoeae | ATCC 49226 | + |
| Neisseria gonorrhoeae | ATCC 51109 | + |
| Non-GC Species: | | |
| Branhamella catarrhalis | ATCC 25238 | − |
| Branhamella catarrhlis | ATCC 25240 | − |
| Chlamydia trachomatis | TYPE B | − |
| Chlamydia trachomatis | TYPE C | − |
| Chlamydia trachomatis | TYPE D | − |
| Chlamydia trachomatis | TYPE J | − |
| Chlamydia trachomatis | TYPE L2 | − |
| Chlamydia trachomatis | TYPE L3 | − |
| Kingella kingae | ATCC 23330 | − |
| Moraxella lacunata | ATCC 17967 | − |
| Neisseria flavescens | ATCC 13120 | − |
| Neisseria lactamica | ATCC 44418 | − |
| Neisseria lactamica | ATCC 23970 | − |
| Neisseria meningitidis | ATCC 13077 | − |
| Neisseria meningitidis | ATCC 13090 | − |
| Neisseria meningitidis | ATCC 14632 | − |
| Neisseria sicca | ATCC 29193 | − |
| Neisseria sicca | ATCC 9913 | − |
| Neisseria subflava | ATCC 14799 | − |

EXAMPLE 6

Sequencing of the GC3 Fragments from Six GC Strains

To determine the degree of sequence homology in the GC3 region across GC strains, the GC3 amplification products were sequenced from six of the GC strains amplified with the GC3-specific PCR amplification primers in Example 5. The six GC strains used for sequencing are shown in Table 3. The PCR amplification products were purified using the Qiagen Qiaex II system (Qiagen; Santa Clarita, Calif.) according to the manufacturer's instructions. Each purified amplified DNA fragment was used as a template for cycle sequencing as described in Example 4. The DNA fragments were sequenced using the GC3-specific primers (GC3-5' and GC3-3') as shown in Example 5.

TABLE 3

GC Strains used as Template for Sequencing of GC3

| GC Strains | ID# |
|---|---|
| Neisseria gonorrhoeae | CDC 111 |
| Neisseria gonorrhoeae | ATCC 19424 |
| Neisseria gonorrhoeae | BDMS 2900 |
| Neisseria gonorrhoeae | ATCC 35541 |
| Neisseria gonorrhoeae | ATCC 43069 |
| Neisseria gonorrhoeae | ATCC 43070 |

The GC3 sequences from the six strains (SEQ ID NO:2 and SEQ ID NO:6 to SEQ ID NO:10) are shown in FIG. 2. The sequences were aligned and a consensus GC3 sequence (SEQ ID NO:5) determined, as shown in FIG. 2. Among the six strains aligned, only one base variant was identified within the 240 bp before the stop codon, indicating a homology of >99.5%. The homology among the sequences after the stop codon was approximately 90%.

EXAMPLE 7

PCR Mapping of the GC3 Region

A series of PCR primers were designed to test the specificity/cross-reactivity of the GC3 DNA fragment. The primer sequences (SEQ ID NO:11 to SEQ ID NO:19) and their relative locations in the GC3 region are illustrated in FIG. 3 (not to scale). The PCR mapping experiments were performed with different primer combinations, as shown below in Table 4.

All primer combinations tested gave positive results with all GC strains. The primer combinations PL1/PR1 (SEQ ID NO:11) and (SEQ ID NO:15) and PL1/PR2 (SEQ ID NO:11 and SEQ ID NO:16) cross-reacted with N. meningitidis. These 3 primers all target the 5' half of the GC3 fragment (i.e., before the stop codon). The primer combinations PR3/BL3 (SEQ ID NO:18) and (SEQ ID NO:13) and PR3/PL3 (SEQ ID NO:18) and (SEQ ID NO:14) cross-reacted with N. lactamica. These 3 primers all target the 3' region of the GC3 fragment (i.e., after the stop codon). The primer combinations PL1/PR3 (SEQ ID NO:11) and (SEQ ID NO:18), PL1/BR3 (SEQ ID NO:11) and (SEQ ID NO:19), PR3/PL2 (SEQ ID NO:18) and (SEQ ID NO:12) as well as the previously tested GC3-5'/GC3-3' (SEQ ID NO:3 and SEQ ID NO:4) primer set did not cross-react with any non-GC species. A common characteristic of all these primer sets is that they have one primer located before the stop codon and the other after the stop codon (see FIG. 3). In summary, these results indicate that any primer set that amplifies across the stop codon is specific for GC.

TABLE 4

PCR Mapping of the GC3 Region

| | NG24[1] | NG26 | NG41 | NG42 | NM77 | NL70 | NF20 | NS93 | NSF43 | BC88 | CTD |
|---|---|---|---|---|---|---|---|---|---|---|---|
| PL1/PR1 | + | + | + | + | + | − | − | − | − | − | − |
| PL1/PR2 | + | + | + | + | + | − | − | − | − | − | − |
| PL1/PR3 | + | + | + | + | − | − | − | − | − | − | − |
| PL1/BR3 | + | + | + | + | − | − | − | − | − | − | − |
| PR3/PL2 | + | + | + | + | − | − | − | − | − | − | − |
| PR3/BL3 | + | + | + | + | − | + | − | − | − | − | − |
| PR3/PL3 | + | nt[2] | + | nt | − | + | − | nt | nt | − | nt |

[1]NG = *N. gonorrhoeae*; NM = *N. meningitidis*; NL = *N. lactamica*; NF = *N. flavescens*; NS = *N. sicca*; NSF = *N. subflava*; BC = *Branhamella catarrhalis*; CTD = *C. trachomatis* type D
[2]nt = not tested

EXAMPLE 8

Thermophilic Strand Displacement Amplification (tSDA) Procedure The tSDA reactions were carried out essentially as previously described in U.S. Pat. No. 5,648,211 and European Application No. EP 0 684 315 to Frasier et al., with substitution of dUTP for TTP to allow for inactivation (decontamination) of amplicons carried over to subsequent reactions using uracil DNA glycosylase (UDG).

For each tSDA reaction, the target DNA was added to a tube containing human placental DNA, DMSO, glycerol, and potassium phosphate. The reaction mixture was boiled for two minutes to denature the DNA and then transferred to a Thermal-lok set at 45° C. The decontamination mix containing potassium phosphate, dGTP, dATP, thio-dCTP, primers, bumpers, BSA, DTT, trehalose, UDG, and magnesium acetate was then added and the mixture incubated for 30 minutes at 45° C. Following the incubation, the amplification mix containing potassium phosphate, dUTP, BSA, DTT, trehalose, UDI, Bso B1, Bst polymerase, and magnesium acetate was added, and the tube incubated at the amplification temperature (52° C.) for 30 minutes. The amplification reaction was stopped by boiling the reaction tube for 5 minutes. This protocol was used in all experiments.

tSDA final reaction mixture (50 μl):
  35 mM Potassium phosphate
  100 μg/ml acetylated bovine serum albumin
  1.4 mM thiodCTP, 0.5 mM dUTP, 0.2 mM dGTP, and 0.2 mM dATP
  6 mM Magnesium Acetate
  0.5 μM and 0.05 μM of tSDA primers and bumpers, respectively
  1000 ng per reaction of human placental DNA
  7% Glycerol
  7% DMSO
  9 units of Bst polymerase
  160 units of Bso B1
  1 unit Uracil-N-glycosylase
  5 units Uracil-N-glycosylase inhibitor
  Temperature: 52° C.

The amplification products are detected with an amplicon specific radiolabeled detection probe in a primer extension reaction as described below in Example 9. Alternatively, the amplification products can be detected by a latex-immunoassay, in which one detector probe is biotinylated and the second is antigen conjugated.

EXAMPLE 9

Radiolabel Extension Reactions

The detection probes were 5'-$^{32}$P-labeled using T4 polynucleotide kinase to facilitate detection of amplification product. The radiolabeling conditions were: 1 mM detector probe oligonucleotide, 30 units T4 DNA polynucleotide kinase, 70 μCi γ-$^{32}$P-ATP, and 1× PNK buffer(10× NK buffer available from United States Biochemical, Inc.). The reactions were allowed to proceed at 37° C. for 45 minutes, and were stopped by heating the samples at 65° C. for 10 minutes. The labeled detection probe was stored at −20° C. and used within one week.

The radiolabel extension reactions were carried out by mixing 5 μl of the tSDA sample with 5 μl of the detection mix containing the radiolabeled detection probe (detection mix=50 mM KPO$_4$, 0.2 mM each α-thio-dATP, dCTP, and dGTP, 0.5 mM dUTP, and 1 μl radiolabeled detection probe). The samples were boiled for 2 minutes, followed by at least 2 minutes of equilibration in a 37° C. waterbath. Enzyme mix (1 μl) was added to each detection reaction and incubated at 37° C. for 10 minutes (enzyme mix=2 units exo- Klenow and 1× React 1 buffer (10× React 1 buffer available from BRL Life Technologies Inc.). Reactions were stopped by the addition of 10 μl stop mix (available from USB; 3×=95% formamide, 20 mM EDTA, 0.05% bromophenol blue, 0.05% xylene cyanol), followed by boiling the samples for 2 minutes. Radiolabeled extension products were detected by separating the reaction products through an 8% polyacrylamide gel followed by autoradiography and quantification with a Molecular Dynamics 455SI phosphoimager and ImageQuant v1.1 software.

EXAMPLE 10

Amplification of GC3 by Thermophilic Strand Displacement Amplification (tSDA)

GC3-specific amplification primers, bumpers, and detection probes were designed for thermophilic Strand Displacement Amplification (tSDA) of GC3 as shown in FIG. 4A. The Bso B1 restriction site in each primer is italicized, and the target binding sequence is underlined. Eight of the 12 possible amplification primer combinations (3 left primers×4 right primers) were screened. All of the primer combinations tested amplify across the stop codon in the GC3 sequence. Positive amplification was observed with all 9 primer combinations. The combination GC3L46N (SEQ ID NO:22) and GC3R44N (SEQ ID NO:24) was chosen for further investigation. The bumpers GC3BL44 (SEQ ID NO:27) and GC3BR46 (SEQ ID NO:28), and the detector GC3D2R (SEQ ID NO:33), as shown in FIG. 4A, were also chosen. The selected GC3 tSDA system is depicted graphically in FIG. 4B. The amplification product is 62 bp in length.

EXAMPLE 11

Sensitivity of the GC3 tSDA System

A genome titration curve was performed to determine the minimum genome copy number that could be amplified and detected by the GC3 tSDA system. GC genomic DNA was isolated and diluted in 10 ng of human placental DNA. tSDA reactions were performed as described in Example 8 using $10^5$, $10^4$, $10^3$, $10^2$, $10^1$ and 0 genome copies per reaction. A sensitivity of 10 genome copies was achieved with $^{32}P$ labeled hairpin detector probes directed against the amplification products.

EXAMPLE 12

Cross-Reactivity of the GC3 tSDA System

Pooled genomic DNA from 42 non-GC species were tested in 11 pools for cross-reactivity with the GC3 tSDA system. Genomic DNA from three to four non- GC species, each at the 107 genome copy level, were pipetted into one tube and amplified using the GC3 tSDA system as shown below and in FIG. 4B.

Primer/Bumper Set: GC3L46N (SEQ ID NO:22), GC3R44N (SEQ ID NO:24), GC3BL44 (SEQ ID NO:27), GC3BR46 (SEQ ID NO:28)

Detector: GC3D2R (SEQ ID NO:33)

To prevent false negatives arising due to amplification inhibition, a control sample was included that contained the non-GC pool with $10^4$ genome copies of GC template added. Eleven such pools (42 species/strains) and their related controls (spikes) were tested. The results are shown below in Table 5. All 11 non-GC pools were negative for amplification by the GC3 tSDA system, while all spiked pool controls were positive.

TABLE 5

Evaluation of the Cross-Reactivity of Non-GC Species (in 11 pools) with the GC tSDA System

| Pool[1,2] | Non-GC Species |
|---|---|
| Pool 1: | *Neisseria subflava* 19243, *Neisseria subflava* 14799, *Branhamella catarrhalis* 25238 |
| Pool 2: | *Neisseria lactamica* 23970, *Neisseria lactamica* 23972, *Neisseria meningitidis* 13077, *Neisseria meningitidis* 13090 |
| Pool 3: | *Staph. aureus* 12598, *Strep.. feacalis* 29212, *Strep.* grpA 16915, *Strep.* grpB 12386 |
| Pool 4: | *Salmonella typhimurium* 13311, *Salmonella minnesota* 9700, *E. coli* 11775, *Klebsiella pneumoniae* 13883 |
| Pool 5: | *Acinetobacter lwoffi* 19901, *Haemophilas influenza* 41433, *Moraxella lacunata* 17967, *Proteus mirabilis* 29906 |
| Pool 6: | *Candida albicans* 44808, *Gardnerella vaginalis* 14018, *Mycoplasma orale* 23714, *Tricomonas vaginalis* 30001 |
| Pool 7: | HSV-1, HSV-2, *Peptostreptococcus productus* 27340 |
| Pool 8: | *Neisseria cinerea* 14685, *Neisseria elongata* 25295, *Neisseria flavescens* 13120, *Neisseria sicca* 29193 |
| Pool 9: | *Brahm. Catarrhalis* 25240, *Kingella kingae* 23330, *Neisseria mucosa* 19696, *Neisseria subflava* 14799 |
| Pool 10: | *Neisseria meningitidis* 13102, *Neisseria meningitidis* 13113, *Neisseria meningitidis* 14632, *Neisseria meningitidis* 35559 |
| Pool 11: | *Neisseria lactamica* 23971, *Neisseria lactamica* 44418, *Neisseria lactamica* 49142, *Neisseria sicca* 9913 |

[1]Each pool includes $10^7$ genomes of each species.
[2]Each control pool is a duplicate sample containing $10^4$ genomes of GC DNA.

EXAMPLE 13

Summary of the GC3 Fragment and GC3 Amplification Systems

1. The GC3 fragment is 414 bp in length.
2. The 7 sequenced GC strains share >99.5% homology in the 5' half of the GC3 fragment before the stop codon, and approximately 90% homology within the 3' half.
3. No Bso B1 restriction site was found in the GC3 fragment.
4. No similar DNA sequence was found among over 600 sequence entries of Neisseria species in GenBank.
5. PCR specificity tests of 12 GC strains were 100% positive.
6. PCR cross-reactivity tests of 19 non-GC species were 100% negative.
7. The sensitivity of the GC3 tSDA system was 10 genomes.
8. tSDA cross-reactivity tests of 42 non-GC species were 100% negative.

Although the foregoing invention has been described in some detail by way of illustration and example for purposes of clarity and understanding, it will be obvious that certain changes and modifications may be practiced within the scope of the appended claims.

That which is claimed is:

1. A method for species-specific detection of *Neisseria gonorrhoeae* nucleic acids comprising the steps of:
   (a) hybridizing to *Neisseria gonorrhoeae* nucleic acids at least two amplification primers, one of said at least two amplification primers comprising a target binding sequence, the target binding sequence consisting of at least 10 consecutive nucleotides of a *Neisseria gonorrhoeae* GC3 sequence selected from the group consisting of SEQ ID NO:2, the complementary sequence of SEQ ID NO:2, SEQ ID NO:5, the complementary sequence of SEQ ID NO:5, SEQ ID NO:6, the complementary sequence of SEQ ID NO:6, SEQ ID NO:7, the complementary sequence of SEQ ID NO:7, SEQ ID NO:8, the complementary sequence of SEQ ID NO:8, SEQ ID NO:9, the complementary sequence of SEQ ID NO:9, SEQ ID NO:10 and the complementary sequence of SEQ ID NO:10; and
   (b) amplifying the *Neisseria gonorrhoeae* nucleic acids with the at least two amplification primers; and
   (c) detecting the amplified *Neisseria gonorrhoeae* nucleic acids.

2. A method according to claim 1, wherein said amplifying step is carried out by extending the at least two amplification primers.

3. A method according to claim 1, wherein the at least two amplification primers further comprise a sequence for amplification of the target nucleic acids.

4. A method according to claim 1, wherein the target binding sequence of the at least two amplification primers are selected from the group consisting of SEQ ID NO:3, SEQ ID NO:4, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, the target binding sequence of SEQ ID NO:20, the target binding sequence of SEQ ID NO:21, the target binding sequence of SEQ ID NO:22, the target binding sequence of SEQ ID NO:23, the target binding sequence of SEQ ID NO:24, the target binding sequence of SEQ ID NO:25, the target binding sequence of SEQ ID NO:26, SEQ ID NO:27, SEQ ID NO:28, SEQ ID NO:29, SEQ ID NO:30, SEQ ID NO:31, SEQ ID NO:32, and SEQ ID NO:33.

5. A method according to claim 4, wherein the target binding sequence of the at least two amplification primers are selected from the group consisting of SEQ ID NO:20, SEQ ID NO:21, SEQ ID NO:22, SEQ ID NO:23, SEQ ID NO:24, SEQ ID NO:25, and SEQ ID NO:26.

6. A method according to claim 1, wherein detection of the amplified *Neisseria gonorrhoeae* nucleic acid is performed with a detection probe which is selected from the group consisting of SEQ ID NO:30, SEQ ID NO:3 1, SEQ ID NO:32, and SEQ ID NO:33.

7. A method according to claim 1,
   wherein the at least two amplification primers are chosen such that one of the at least two amplification primers hybridizes to a *Neisseria gonorrhoeae* GC3 sequence at a position 5' of the stop codon sequence, and the other of the at least two amplification primers hybridizes to the *Neisseria gonorrhoeae* GC3 sequence at a position 3' of the GC3 stop codon.

8. A method according to claim 7, wherein:
   (a) a first amplification primer has a sequence selected from the group consisting of SEQ ID NO:3, SEQ ID NO:11 and SEQ ID NO:12, and a second amplification primer has a sequence selected from the group consisting of SEQ ID NO:4, SEQ ID NO:17, SEQ ID NO:18 and SEQ ID NO:19; or
   (b) a first amplification primer has a sequence selected from the group consisting of SEQ ID NO:15 and SEQ ID NO:16, and a second amplification primer has a sequence selected from the group consisting of SEQ ID NO:13 and SEQ ID NO:14.

9. A method according to claim 7, wherein first and second amplification primers are selected from the group consisting of:
   (a) SEQ ID NO:3 and SEQ ID NO:4; and
   (b) SEQ ID NO:11 and SEQ ID NO:18; and
   (c) SEQ ID NO:11 and SEQ ID NO:19; and
   (d) SEQ ID NO:18 and SEQ ID NO:12.

10. A method for detection of *Neisseria gonorrhoeae* nucleic acids comprising the steps of:
    (a) hybridizing to *Neisseria gonorrhoeae* nucleic acids a first and a second amplification primer, each of the first and second amplification primers comprising a target binding sequence and a sequence for amplification of the target nucleic acids, wherein the target binding sequence of the first amplification primer is selected from the group consisting of the target binding sequences of SEQ ID NO:20, SEQ ID NO:21, and SEQ ID NO:22, and wherein the target binding sequence of the second amplification primer is selected from the group consisting of the target binding sequences of SEQ ID NO:23, SEQ ID NO:24, SEQ ID NO:25, and SEQ ID NO:26; and (b) extending the hybridized first and second amplification primers on the *Neisseria gonorrhoeae* target nucleic acids, whereby the target nucleic acid is amplified; and (c) detecting the amplified *Neisseria gonorrhoeae* nucleic acids.

11. A method according to claim 10, wherein the first amplification primer is selected from the group consisting of SEQ ID NO:20, SEQ ID NO:21 and SEQ ID NO:22, and wherein the second amplification primer is selected from the group consisting of SEQ ID NO:23, SEQ ID NO:24, SEQ ID NO:25, and SEQ ID NO:26.

12. A method according to claim 11, wherein the first amplification primer is SEQ ID NO:22 and the second amplification primer is SEQ ID NO:24.

13. A method according to claim 10, wherein said hybridizing step further comprises hybridizing a first and a second bumper primer to the *Neisseria gonorrhoeae* nucleic acids, wherein the first bumper primer has a sequence consisting of SEQ ID NO:27 and the second bumper primer is selected from the group consisting of SEQ ID NO:28 and SEQ ID NO:29.

14. An isolated DNA consisting of a *Neisseria gonorrhoeae* GC3 sequence selected from the group consisting of SEQ ID NO:2, the complementary sequence of SEQ ID NO:2, SEQ ID NO:5, the complementary sequence of SEQ ID NO:5, SEQ ID NO:6, the complementary sequence of SEQ ID NO:6, SEQ ID NO:7, the complementary sequence of SEQ ID NO:7, SEQ ID NO:8, the complementary sequence of SEQ ID NO:8, SEQ ID NO:9, the complementary sequence of SEQ ID NO:9, SEQ ID NO:10 and the complementary sequence of SEQ ID NO:10.

15. An oligonucleotide comprising a sequence selected from the group consisting of SEQ ID NO:3, SEQ ID NO:11, SEQ ID NO:12, SEQ ID NO:13, SEQ ID NO:15, SEQ ID NO:16, SEQ ID NO:17, the target binding sequence of SEQ ID NO:20, the target binding sequence of SEQ ID NO:21, the target binding sequence of SEQ ID NO:22, the target binding sequence of SEQ ID NO:23, the target binding sequence of SEQ ID NO:24, the target binding sequence of SEQ ID NO:25, the target binding sequence of SEQ ID NO:26, SEQ ID NO:27, SEQ ID NO:28, SEQ ID NO:29, SEQ ID NO:30, and SEQ ID NO:31.

16. An oligonucleotide according to claim 15, wherein said oligonucleotide further comprises a sequence for amplification of a target nucleic acid.

17. An oligonucleotide according to claim 16, wherein said oligonucleotide is selected from the group consisting of SEQ ID NO:20, SEQ ID NO:21, SEQ ID NO:22, SEQ ID NO:23, SEQ ID NO:24, SEQ ID NO:25, and SEQ ID NO:26.

18. A primer set which specifically amplifies *Neisseria gonorrhoeae* nucleic acids comprising a first amplification primer comprising a target binding sequence consisting of at least 10 consecutive nucleotides of an isolated DNA according to claim 14.

19. A primer set according to claim 18, wherein said first amplification primer is selected from, the group consisting of SEQ ID NO:3, SEQ ID NO:4, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, the target binding sequence of SEQ ID NO:20, the target binding sequence of SEQ ID NO:21, the target binding sequence of SEQ ID NO:22, the target binding sequence of SEQ ID NO:23, the target binding sequence of SEQ ID NO:24, the target binding sequence of SEQ ID NO:25, the target binding sequence of SEQ ID NO:26, SEQ ID NO:27, SEQ ID NO:28, SEQ ID NO:29, SEQ ID NO:30, SEQ ID NO:31, SEQ ID NO:32, and SEQ ID NO:33.

20. A primer set according to claim 18 further comprising a second amplification primer comprising a target binding sequence consisting of at least 10 consecutive nucleotides of a *Neisseria gonorrhoeae* GC3 sequence selected from the group consisting of SEQ ID NO:2, the complementary sequence of SEQ ID NO:2, SEQ ID NO:5, the complementary sequence of SEQ ID NO:5, SEQ ID NO:6, the complementary sequence of SEQ ID NO:6, SEQ ID NO:7, the complementary sequence of SEQ ID NO:7, SEQ ID NO:8, the complementary sequence of SEQ ID NO:8, SEQ ID NO:9, the complementary sequence of SEQ ID NO:9, SEQ ID NO:10, and the complementary sequence of SEQ ID NO:10;

wherein one of said first and second amplification primers specifically hybridizes to a *Neisseria gonorrhoeae* GC3 sequence at a position 5' of the stop codon sequence, and the other of said first and second amplification primers specifically hybridizes to said *Neisseria gonorrhoeae* GC3 sequence at a position 3' of the GC3 stop codon.

21. A primer set according to claim 20 wherein:

(a) said first amplification primer has a sequence selected from the group consisting of SEQ ID NO:3, SEQ ID NO:11 and SEQ ID NO:12, and said second amplification primer has a sequence selected from the group consisting of SEQ ID NO:4, SEQ ID NO:17, SEQ ID NO:18, and SEQ ID NO:19; or (b) said first amplification primer has a sequence selected from the group consisting of SEQ ID NO:15 and SEQ ID NO:16, and said second amplification primer has a sequence selected from the group consisting of SEQ ID NO:13 and SEQ ID NO:14.

22. A primer set according to claim 21, wherein said first and second amplification primers are selected from the group consisting of:

(a) SEQ ID NO:3 and SEQ ID NO:4;

(b) SEQ ID NO:11 and SEQ ID NO:18;

(c) SEQ ID NO:11 and SEQ ID NO:19;

(d) and SEQ ID NO:18 and SEQ ID NO:12.

23. A primer set according to claim 18, wherein said first amplification primer further comprises a sequence for amplification of the target nucleic acids.

24. A primer set according to claim 23, wherein said first amplification primer is selected from the group consisting of SEQ ID NO:20, SEQ ID NO:21, SEQ ID NO:22, SEQ ID NO:23, SEQ ID NO:24, SEQ ID NO:25, and SEQ ID NO:26.

25. A primer set according to claim 24 further comprising a first bumper primer having a sequence consisting of SEQ ID NO:27 and a second bumper primer having a sequence selected from the group consisting of SEQ ID NO:28 and SEQ ID NO:29.

26. A primer set according to claim 24, wherein said first amplification primer is selected from the group consisting of SEQ ID NO:20, SEQ ID NO:21, and SEQ ID NO:22. and a second amplification primer is selected from the group consisting of SEQ ID NO:23, SEQ ID NO:24, SEQ ID NO:25, and SEQ ID NO:26.

27. A primer set according to claim 26, wherein said first amplification primer is SEQ ID NO:22 and said second amplification primer is SEQ ID NO:24.

28. A primer set for species-specific amplification of *Neisseria gonorrhoeae* nucleic acids comprising a first amplification primer consisting of SEQ ID NO:22, a second amplification primer consisting of SEQ ID NO:24, a first bumper primer consisting of SEQ ID NO:27, and a second bumper primer consisting of SEQ ID NO:28.

29. A kit for detection of *Neisseria gonorrhoeae* nucleic acids comprising:
   (a) an oligonucleotide according to claims 14, 15 or 16; and
   (b) means for detecting said *Neisseria gonorrhoeae* nucleic acids.

30. A kit for detection of *Neisseria gonorrhoeae* nucleic acids comprising:
   (a) a set of primers for detection of *Neisseria gonorrhoeae* nucleic acids according to claims 18 or 23; and
   (b) means for detecting said *Neisseria gonorrhoeae* nucleic acids.

31. A method for detection of *Neisseria gonorrhoeae* nucleic acids comprising the steps of:
   (a) hybridizing an oligonucleotide probe to *Neisseria gonorrhoeae* nucleic acids, the probe comprising a *Neisseria gonorrhoeae* GC3 sequence selected from the group consisting of SEQ ID NO:2, the complementary sequence of SEQ ID NO:2, SEQ ID NO:5, the complementary sequence of SEQ ID NO:5, SEQ ID NO:6, the complementary sequence of SEQ ID NO:6, SEQ ID NO:7, the complementary sequence of SEQ ID NO:7, SEQ ID NO:8, the complementary sequence of SEQ ID NO:8, SEQ ID NO:9, the complementary sequence of SEQ ID NO:9, SEQ ID NO:10, and the complementary sequence of SEQ ID NO:10; and
   (b) detecting hybridization between the oligonucleotide probe and the *Neisseria gonorrhoeae* nucleic acids.

32. A method according to claim 31, wherein said detecting step is carried out by detecting a detectable label bound to the oligonucleotide probe.

33. A method for detection of *Neisseria gonorrhoeae* nucleic acids comprising the steps of:
   (a) hybridizing an oligonucleotide probe to *Neisseria gonorrhoeae* nucleic acids, the probe consisting of a sequence selected from the group consisting of SEQ ID NO:3, SEQ ID NO:11, SEQ ID NO:12, SEQ ID NO:13, SEQ ID NO:14, SEQ ID NO:15, SEQ ID NO:16, SEQ ID NO:17, SEQ ID NO:18, the target binding sequence of SEQ ID NO:20, the target binding sequence of SEQ ID NO:21, the target binding sequence of SEQ ID NO:22, the target binding sequence of SEQ ID NO:23, the target binding sequence of SEQ ID NO:24, the target binding sequence of SEQ ID NO:25, the target binding sequence of SEQ ID NO:26, SEQ ID NO:27, SEQ ID NO:28, SEQ ID NO:29, SEQ ID NO:30, SEQ ID NO:31, SEQ ID NO:32, and SEQ ID NO:33; and
   (b) detecting hybridization between the oligonucleotide probe and the *Neisseria gonorrhoeae* nucleic acids.

34. A method for detection of *Neisseria gonorrhoeae* nucleic acids comprising the steps of:
   (a) hybridizing an oligonucleotide probe to *Neisseria gonorrhoeae* nucleic acids, the probe comprising a sequence selected from the group consisting of SEQ ID NO:3, SEQ ID NO:11, SEQ ID NO:12, SEQ ID NO:13, SEQ ID NO:15, SEQ ID NO:16, SEQ ID NO:17, the target binding sequence of SEQ ID NO:20, the target binding sequence of SEQ ID NO:21, the target binding sequence of SEQ ID NO:22, the target binding sequence of SEQ ID NO:23, the target binding sequence of SEQ ID NO:24, the target binding sequence of SEQ ID NO:25, the target binding sequence of SEQ ID NO:26, SEQ ID NO:27, SEQ ID NO:28, SEQ ID NO:29, SEQ ID NO:30, and SEQ ID NO:3 1; and
   (b) detecting hybridization between the oligonucleotide probe and the *Neisseria gonorrhoeae* nucleic acids.

* * * * *

SEQUENCE LISTING (1) GENERAL INFORMATION:

(iii) NUMBER OF SEQUENCES: 33

(2) INFORMATION FOR SEQ ID NO:1:

(i) SEQUENCE CHARACTERISTICS:
      (A) LENGTH: 19 base pairs
      (B) TYPE: nucleic acid
      (C) STRANDEDNESS: single
      (D) TOPOLOGY: linear (ii) MOLECULE TYPE: other nucleic acid (xi) SEQUENCE DESCRIPTION: SEQ ID NO:1:

CGGTTGCCTC CATGCAGAT                  19

(2) INFORMATION FOR SEQ ID NO:2:

(i) SEQUENCE CHARACTERISTICS:
        (A) LENGTH: 414 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: GC strain ATCC 19424

(xi) SEQUENCE DESCRIPTION: SEQ ID NO:2:

```
CGGCATACTG TACCATAGCG TTCGCCTGGT CCGCCAAACG GGAAATTGGC GGCATAAGCA     60

GGGAACTGCT CCTGCAAACC TTTGACGACA TTTTGATCTT CATAAAACAA AATGGTTGCC    120

GCGCCCACCT TAAACAGCTT CAATTTTTGC GCGGTCGGTT CAAAACTGTC GGCAGGCACG    180

ACGGCACGCA GCGCGTCTTC GACAAATTGC CACACCTTAT ATATTGCGCC CCTTCTTAGG    240

GACGCAATAT ATAAGGGTAA TCCCATGCGT AACGCCGTAG GATTGGACAT ATCCAAGTTG    300

ACTTTTGACG CAACGGCCAT TGTCGGCAAT GCCGAATATT CGGCAAAGTT TGACAACGAT    360

TCAAAAGGTT TAGATCAGTT TTCGGACCGG TTGAAAAGCT TGGGATGTCA GAAT          414
```

(2) INFORMATION FOR SEQ ID NO:3:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:3:

```
CATACTGTAC CATAGCGTT                                                  19
```

(2) INFORMATION FOR SEQ ID NO:4:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:4:

```
ATTCTGACAT CCCAAGCTT                                                  19
```

(2) INFORMATION FOR SEQ ID NO:5:

(i) SEQUENCE CHARACTERISTICS:
        (A) LENGTH: 414 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Consensus GC3 sequence (xi) SEQUENCE DESCRIPTION: SEQ ID NO:5:

```
CGGCATACTG TACCATAGCG TTCGCCTGGT CCGCCAAACG GGAAATTGGC GGCATAAGCA     60

GGGAACTGCT CCTGCAAACC TTTGACGACA TTTTGATCTT CATAAAACAA AATGGTTGCC    120
```

```
GCGCCCRCCT TAAACAGCTT CAATTTTTGC GCGGTCGGTT CAAAACTGTC GGCAGGCACG        180

ACGGCACGCA GCGCGTCTTC GACAAATTGC CACACCTTAT ATATTGCGCC CCTTCTTAGG        240

GACGCAATAT ATAAGGGTAA TCCCATGCGT AACRCCGTAG GATTGGAYAT ATCSAARYTG        300

ACHTTTRACG CAWCSGCCAT KGTCGGCAAW RCSGARYATT CGGCAAAGTT TGACAACGAT        360

TCAAAAGGTT TAGATCAGTT TTCGGACCGG TTGAAAAGCT TGGGATGTCA GAAT             414

(2) INFORMATION FOR SEQ ID NO:6:

(i) SEQUENCE CHARACTERISTICS:
            (A) LENGTH: 414 base pairs
            (B) TYPE: nucleic acid
            (C) STRANDEDNESS: double
            (D) TOPOLOGY: linear (ii) MOLECULE TYPE: DNA (genomic)

(vi) ORIGINAL SOURCE:
            (A) ORGANISM: GC strain ATCC 35541

(xi) SEQUENCE DESCRIPTION: SEQ ID NO:6:

CGGCATACTG TACCATAGCG TTCGCCTGGT CCGCCAAACG GGAAATTGGC GGCATAAGCA        60

GGGAACTGCT CCTGCAAACC TTTGACGACA TTTTGATCTT CATAAAACAA AATGGTTGCC       120

GCGCCCGCCT TAAACAGCTT CAATTTTTGC GCGGTCGGTT CAAAACTGTC GGCAGGCACG       180

ACGGCACGCA GCGCGTCTTC GACAAATTGC CACACCTTAT ATATTGCGCC CCTTCTTAGG       240

GACGCAATAT ATAAGGGTAA TCCCATGCGT AACACCGTAG GATTGGACAT ATCCAAGCTG       300

ACATTTGACG CAACGGCCAT TGTCGGCAAT GCCGAATATT CGGCAAAGTT TGACAACGAT       360

TCAAAAGGTT TAGATCAGTT TTCGGACCGG TTGAAAAGCT TGGGATGTCA GAAT             414

(2) INFORMATION FOR SEQ ID NO:7:

(i) SEQUENCE CHARACTERISTICS:
            (A) LENGTH: 414 base pairs
            (B) TYPE: nucleic acid
            (C) STRANDEDNESS: double
            (D) TOPOLOGY: linear (ii) MOLECULE TYPE: DNA (genomic)

(vi) ORIGINAL SOURCE:
            (A) ORGANISM: GC strain ATCC 43069

(xi) SEQUENCE DESCRIPTION: SEQ ID NO:7:

CGGCATACTG TACCATAGCG TTCGCCTGGT CCGCCAAACG GGAAATTGGC GGCATAAGCA        60

GGGAACTGCT CCTGCAAACC TTTGACGACA TTTTGATCTT CATAAAACAA AATGGTTGCC       120

GCGCCCGCCT TAAACAGCTT CAATTTTTGC GCGGTCGGTT CAAAACTGTC GGCAGGCACG       180

ACGGCACGCA GCGCGTCTTC GACAAATTGC CACACCTTAT ATATTGCGCC CCTTCTTAGG       240

GACGCAATAT ATAAGGGTAA TCCCATGCGT AACACCGTAG GATTGGACAT ATCCAAGCTG       300

ACATTTGACG CATCCGCCAT GGTCGGCAAA ACGGAGCATT CGGCAAAGTT TGACAACGAT       360

TCAAAAGGTT TAGATCAGTT TTCGGACCGG TTGAAAAGCT TGGGATGTCA GAAT             414

(2) INFORMATION FOR SEQ ID NO:8:

(i) SEQUENCE CHARACTERISTICS:
            (A) LENGTH: 414 base pairs
            (B) TYPE: nucleic acid
            (C) STRANDEDNESS: double
            (D) TOPOLOGY: linear (ii) MOLECULE TYPE: DNA (genomic)
```

(vi) ORIGINAL SOURCE:
    (A) ORGANISM: GC strain ATCC 43070

(xi) SEQUENCE DESCRIPTION: SEQ ID NO:8:

```
CGGCATACTG TACCATAGCG TTCGCCTGGT CCGCCAAACG GGAAATTGGC GGCATAAGCA      60
GGGAACTGCT CCTGCAAACC TTTGACGACA TTTTGATCTT CATAAAACAA AATGGTTGCC     120
GCGCCCGCCT TAAACAGCTT CAATTTTTGC GCGGTCGGTT CAAAACTGTC GGCAGGCACG     180
ACGGCACGCA GCGCGTCTTC GACAAATTGC CACACCTTAT ATATTGCGCC CCTTCTTAGG     240
GACGCAATAT ATAAGGGTAA TCCCATGCGT AACACCGTAG GATTGGACAT ATCCAAGCTG     300
ACATTTGACG CATCCGCCAT GGTCGGCAAA ACGGAGCATT CGGCAAAGTT TGACAACGAT     360
TCAAAAGGTT TAGATCAGTT TTCGGACCGG TTGAAAAGCT TGGGATGTCA GAAT           414
```

(2) INFORMATION FOR SEQ ID NO:9:

(i) SEQUENCE CHARACTERISTICS:
        (A) LENGTH: 414 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: GC strain BDMS2900

(xi) SEQUENCE DESCRIPTION: SEQ ID NO:9:

```
CGGCATACTG TACCATAGCG TTCGCCTGGT CCGCCAAACG GGAAATTGGC GGCATAAGCA      60
GGGAACTGCT CCTGCAAACC TTTGACGACA TTTTGATCTT CATAAAACAA AATGGTTGCC     120
GCGCCCGCCT TAAACAGCTT CAATTTTTGC GCGGTCGGTT CAAAACTGTC GGCAGGCACG     180
ACGGCACGCA GCGCGTCTTC GACAAATTGC CACACCTTAT ATATTGCGCC CCTTCTTAGG     240
GACGCAATAT ATAAGGGTAA TCCCATGCGT AACGCCGTAG GATTGGATAT ATCGAAACTG     300
ACCTTTAACG CATCCGCCAT TGTCGGCAAT GCCGAATATT CGGCAAAGTT TGACAACGAT     360
TCAAAAGGTT TAGATCAGTT TTCGGACCGG TTGAAAAGCT TGGGATGTCA GAAT           414
```

(2) INFORMATION FOR SEQ ID NO:10:

(i) SEQUENCE CHARACTERISTICS:
        (A) LENGTH: 414 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: GC strain CDC 111

(xi) SEQUENCE DESCRIPTION: SEQ ID NO:10:

```
CGGCATACTG TACCATAGCG TTCGCCTGGT CCGCCAAACG GGAAATTGGC GGCATAAGCA      60
GGGAACTGCT CCTGCAAACC TTTGACGACA TTTTGATCTT CATAAAACAA AATGGTTGCC     120
GCGCCCGCCT TAAACAGCTT CAATTTTTGC GCGGTCGGTT CAAAACTGTC GGCAGGCACG     180
ACGGCACGCA GCGCGTCTTC GACAAATTGC CACACCTTAT ATATTGCGCC CCTTCTTAGG     240
GACGCAATAT ATAAGGGTAA TCCCATGCGT AACACCGTAG GATTGGACAT ATCCAAGCTG     300
ACATTTGACG CATCCGCCAT GGTCGGCAAA ACGGAGCATT CGGCAAAGTT TGACAACGAT     360
TCAAAAGGTT TAGATCAGTT TTCGGACCGG TTGAAAAGCT TGGGATGTCA GAAT           414
```

(2) INFORMATION FOR SEQ ID NO:11:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:11:

GCTCCTGCAA ACCTT         15

(2) INFORMATION FOR SEQ ID NO:12:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:12:

CGGCAGGCAC GAC         13

(2) INFORMATION FOR SEQ ID NO:13:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:13:

GCCATTGTCG GCAA         14

(2) INFORMATION FOR SEQ ID NO:14:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:14:

ATTCGGCAAA GTTTGA         16

(2) INFORMATION FOR SEQ ID NO:15:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:15:

CGCGGCAACC ATTT         14

(2) INFORMATION FOR SEQ ID NO:16:

(i) SEQUENCE CHARACTERISTICS:
        (A) LENGTH: 17 base pairs (B) TYPE: nucleic acid
            (C) STRANDEDNESS: single
            (D) TOPOLOGY: linear (ii) MOLECULE TYPE: other nucleic acid (xi) SEQUENCE DESCRIPTION: SEQ ID NO:16:

GCAATATATA AGGTGTG                                                    17

(2) INFORMATION FOR SEQ ID NO:17:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: other nucleic acid (xi) SEQUENCE DESCRIPTION: SEQ ID NO:17:

CTTATATATT GCGTCC                                                     16

(2) INFORMATION FOR SEQ ID NO:18:

(i) SEQUENCE CHARACTERISTICS:
            (A) LENGTH: 14 base pairs
            (B) TYPE: nucleic acid
            (C) STRANDEDNESS: single
            (D) TOPOLOGY: linear (ii) MOLECULE TYPE: other nucleic acid (xi) SEQUENCE DESCRIPTION: SEQ ID NO:18:

TTCAACCGGT CCGA                                                       14

(2) INFORMATION FOR SEQ ID NO:19:

(i) SEQUENCE CHARACTERISTICS:
            (A) LENGTH: 14 base pairs
            (B) TYPE: nucleic acid
            (C) STRANDEDNESS: single
            (D) TOPOLOGY: linear (ii) MOLECULE TYPE: other nucleic acid (xi) SEQUENCE DESCRIPTION: SEQ ID NO:19:

CTGACATCCC AAGC                                                       14

(2) INFORMATION FOR SEQ ID NO:20:

(i) SEQUENCE CHARACTERISTICS:
            (A) LENGTH: 37 base pairs
            (B) TYPE: nucleic acid
            (C) STRANDEDNESS: single
            (D) TOPOLOGY: linear (ii) MOLECULE TYPE: other nucleic acid (xi) SEQUENCE DESCRIPTION: SEQ ID NO:20:

CGATTCCGCT CCAGACTTCT CGGGCTTCTT AGGGACG                              37

(2) INFORMATION FOR SEQ ID NO:21:

(i) SEQUENCE CHARACTERISTICS:
            (A) LENGTH: 38 base pairs
            (B) TYPE: nucleic acid
            (C) STRANDEDNESS: single
            (D) TOPOLOGY: linear (ii) MOLECULE TYPE: other nucleic acid

EQUENCE DESCRIPTION: SEQ ID NO:21:

CGATTCCGCT CCAGACTTCT CGGGCTTCTT AGGGACGC					38

(2) INFORMATION FOR SEQ ID NO:22:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:22:

CGATTCCGCT CCAGACTTCT CGGGCTTCTT AGGGACGCA					39

(2) INFORMATION FOR SEQ ID NO:23:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:23:

ACCGCATCGA ATGCATGTCT CGGGGATATG TCCAATCCT					39

(2) INFORMATION FOR SEQ ID NO:24:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:24:

ACCGCATCGA ATGCATGTCT CGGGGATATG TCCAATCCTA					40

(2) INFORMATION FOR SEQ ID NO:25:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:25:

ACCGCATCGA ATGCATGTCT CGGGGATATG TCCAATCCTA C					41

(2) INFORMATION FOR SEQ ID NO:26:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:26:

ACCGCATCGA ATGCATGTCT CGGGATATGT CCAATCCTAC					40

(2) INFORMATION FOR SEQ ID NO:27:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:27:

AATTGCCACA CCTTAT                                        16

(2) INFORMATION FOR SEQ ID NO:28:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:28:

GATGCGTCAA ATGTCA                                        16

(2) INFORMATION FOR SEQ ID NO:29:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:29:

GGATGCGTCA AATGTCA                                      17

(2) INFORMATION FOR SEQ ID NO:30:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:30:

CGCAATATAT AAGGGT                                        16

(2) INFORMATION FOR SEQ ID NO:31:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:31:

ACCCTTATAT ATTGCG                                        16

(2) INFORMATION FOR SEQ ID NO:32:

(i) SEQUENCE CHARACTERISTICS:
        (A) LENGTH: 15 base pairs

```
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:32:

AATCCCATGC GTAAC                                                   15

(2) INFORMATION FOR SEQ ID NO:33:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:33:

GTTACGCATG GGATT                                                   15
```